US012685520B2

(12) United States Patent
Sauer

(10) Patent No.: US 12,685,520 B2
(45) Date of Patent: Jul. 21, 2026

(54) STERNAL ASCENDER APPARATUS

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 61 days.

(21) Appl. No.: 18/947,455

(22) Filed: Nov. 14, 2024

(65) Prior Publication Data

US 2025/0064442 A1      Feb. 27, 2025

Related U.S. Application Data

(63) Continuation-in-part of application No. 18/110,619, filed on Feb. 16, 2023, now Pat. No. 12,458,336, which is a continuation-in-part of application No. 16/999,838, filed on Aug. 21, 2020, now Pat. No. 11,666,317.

(60) Provisional application No. 63/598,753, filed on Nov. 14, 2023, provisional application No. 63/311,320, filed on Feb. 17, 2022, provisional application No. 62/889,690, filed on Aug. 21, 2019, provisional application No. 62/916,591, filed on Oct. 17, 2019, provisional application No. 62/989,044, filed on Mar. 13, 2020.

(51) Int. Cl.
*A61B 17/02* (2006.01)

(52) U.S. Cl.
CPC ................................ *A61B 17/0218* (2013.01)

(58) Field of Classification Search
CPC ............ A61B 17/0206; A61B 17/0218; A61B 17/0281
See application file for complete search history.

(56) References Cited

U.S. PATENT DOCUMENTS

| | | | |
|---|---|---|---|
| 11,517,298 B2* | 12/2022 | Sauer ................. | A61B 17/0206 |
| 2002/0115909 A1* | 8/2002 | Bolser .............. | A61B 17/00008 |
| | | | 600/210 |
| 2005/0075643 A1* | 4/2005 | Schwab ................ | A61F 2/4611 |
| | | | 606/90 |
| 2015/0209022 A1* | 7/2015 | Ruppert ............. | A61B 17/0206 |
| | | | 600/219 |
| 2015/0305732 A1* | 10/2015 | Dahl ...................... | A61B 17/02 |
| | | | 600/219 |
| 2017/0020494 A1* | 1/2017 | Ross ..................... | A61B 18/148 |
| 2018/0200508 A1* | 7/2018 | Sauer ..................... | A61N 1/372 |
| 2020/0129200 A1* | 4/2020 | Wongsiri ........... | A61B 17/0218 |
| 2020/0345339 A1* | 11/2020 | Radl ................... | A61B 17/0206 |
| 2023/0078407 A1* | 3/2023 | Catania .............. | A61B 17/0206 |
| | | | 600/210 |
| 2023/0172601 A1* | 6/2023 | Sauer, Md ............. | A61B 90/50 |
| | | | 600/235 |

(Continued)

*Primary Examiner* — Nicholas W Woodall
(74) *Attorney, Agent, or Firm* — Michael E. Coyne

(57) ABSTRACT

A sternal elevator apparatus is disclosed. The sternal elevator may include a panel, a support beam traversing the panel, and a post coupled to a proximal end of the panel. The apparatus may also include an indicator handle coupled to the sternal elevator, an actuator drive pivotably coupled to the indicator handle, and a housing movably coupled to the actuator drive. The sternal elevator apparatus may have an actuator drive incorporating a linear rack. The housing further may include a cylindrical gear where the cylindrical gear is engaged with the linear rack.

13 Claims, 34 Drawing Sheets

(56)  References Cited

U.S. PATENT DOCUMENTS

2023/0200797 A1*  6/2023  Sauer ................. A61B 17/0218
                                                          600/204
2025/0032109 A1*  1/2025  Butterfield ......... A61B 17/0206

* cited by examiner

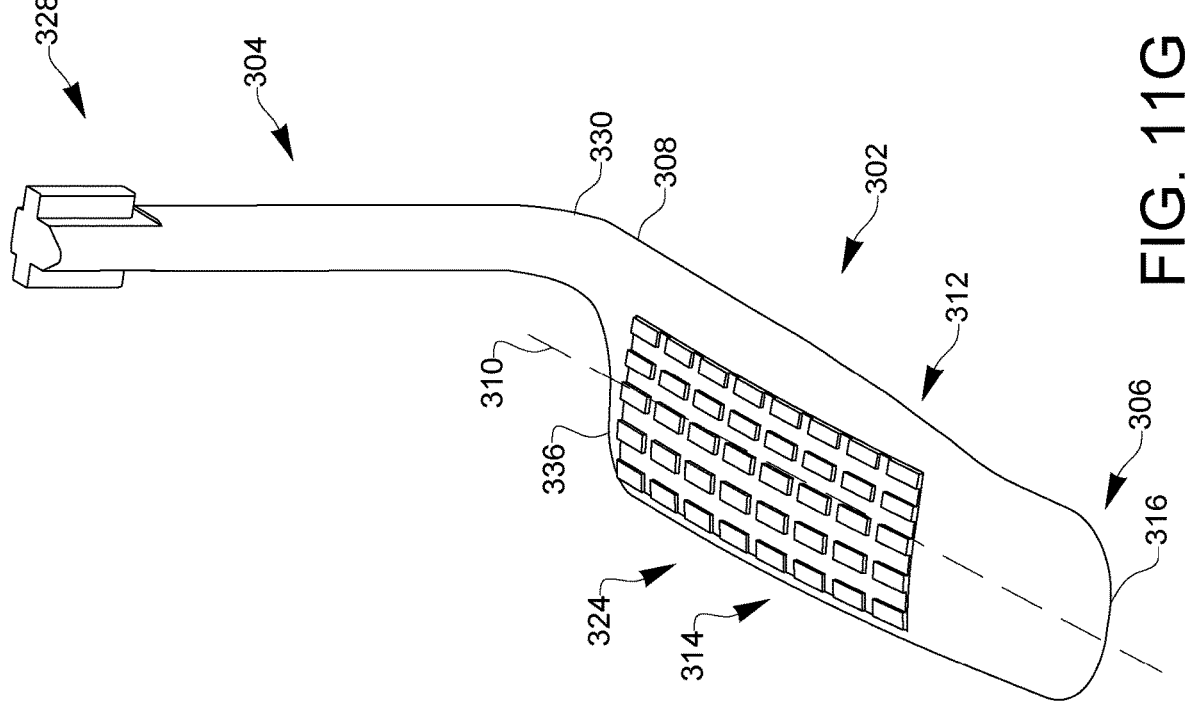
FIG. 11G
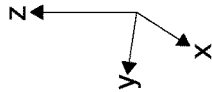

STERNAL ASCENDER APPARATUS

REFERENCE TO RELATED APPLICATIONS

This patent application claims priority to U.S. Provisional Patent Application. No. 63/598,753, filed Nov. 14, 2023, which is hereby incorporated by reference in its entirety. This patent application is a continuation-in-part of U.S. patent application Ser. No. 18/110,619, filed Feb. 16, 2023, which claims priority to U.S. Provisional Patent Application No. 63/311,320, filed Feb. 17, 2022, each of which is hereby incorporated by reference in its entirety. U.S. patent application Ser. No. 18/110,619 is a continuation-in-part of U.S. patent application Ser. No. 16/999,838, filed Aug. 21, 2020, which claims priority to U.S. Provisional Patent Application No. 62/889,690, filed Aug. 21, 2019, U.S. Provisional Patent Application No. 62/916,591, filed Oct. 17, 2019, and U.S. Provisional Patent Application No. 62/989,044, filed Mar. 13, 2020, each of which is hereby incorporated by reference in its entirety.

FIELD

The claimed invention relates to minimally invasive surgical devices, and more specifically to a surgical device used in increasing operable space during minimally invasive surgical procedures.

BACKGROUND

Minimally invasive surgical approaches are gaining increased interest in relation to coronary procedures. Coronary revascularization procedures such as the grafting of the internal thoracic artery (ITA) has shown superior long-term patency and improved patient outcome in coronary artery bypass graft (CABG) surgeries. While conventional approaches to ITA harvesting have included median sternotomy or multiple thoracoports, a minimally invasive approach is desirable. A minimally invasive procedure related to revascularization using either the left or right internal thoracic artery (ITA), or the left or right internal mammary artery (IMA) may utilize access to the ITAs via sub-xiphoid access, where increased surgical space is gained by accessing the internal thoracic arteries via incision at the subxiphocostal region.

Upon harvesting either the left internal thoracic artery (LITA) or the right internal thoracic artery (RITA) anastomoses to the left anterior descending (LAD) coronary artery and to the right coronary artery (RCA), respectively, can be performed without cardiopulmonary bypass (CPB). A significant advantage of this approach is that a perfectly harvested ITA graft can be perfectly anastomosed to the usual site on the LAD artery, or onto the RCA artery. A minimally invasive ITA harvesting procedure involving sub-xiphoid access also results in superior cosmetic results, is reasonably painless, and the arterial grafting can be accomplished on the beating heart. Recent approaches of minimally invasive ITA harvesting surgical techniques have been shown to result in increased effective length of ITA bypasses, reduced operation times, and improved patient recovery.

While less invasive surgical approaches for ITA harvesting and CABG have shown promise, visualization, maintenance of insufflation, and distal suturing of a coronary anastomosis in totally endoscopic coronary artery bypass grafting on the beating heart is technically demanding. There is a need for larger working spaces to accommodate an increased range of motion during surgical procedures, as well as room for additional surgical tools, such as endoscopes, suturing tools, and the like. However, achieving an increased working space should ideally preserve chest wall integrity and avoid CPB. Likewise, a minimally invasive surgical approach should not compromise the reliability of a cardiac repair.

Therefore, there exists a need for minimally invasive surgical devices and methodology applicable to ITA harvesting and other surgical procedures such as epicardial lead placement and others that increase operable space for harvesting and anastomosis and other surgical procedures, reduce operating time, and improve patient outcome during minimally invasive cardiac procedures and other surgical procedures.

BRIEF DESCRIPTION OF THE DRAWINGS

FIG. 11G is a first perspective view of the embodiment of the panel member of FIG. 11A.

Figure 1:
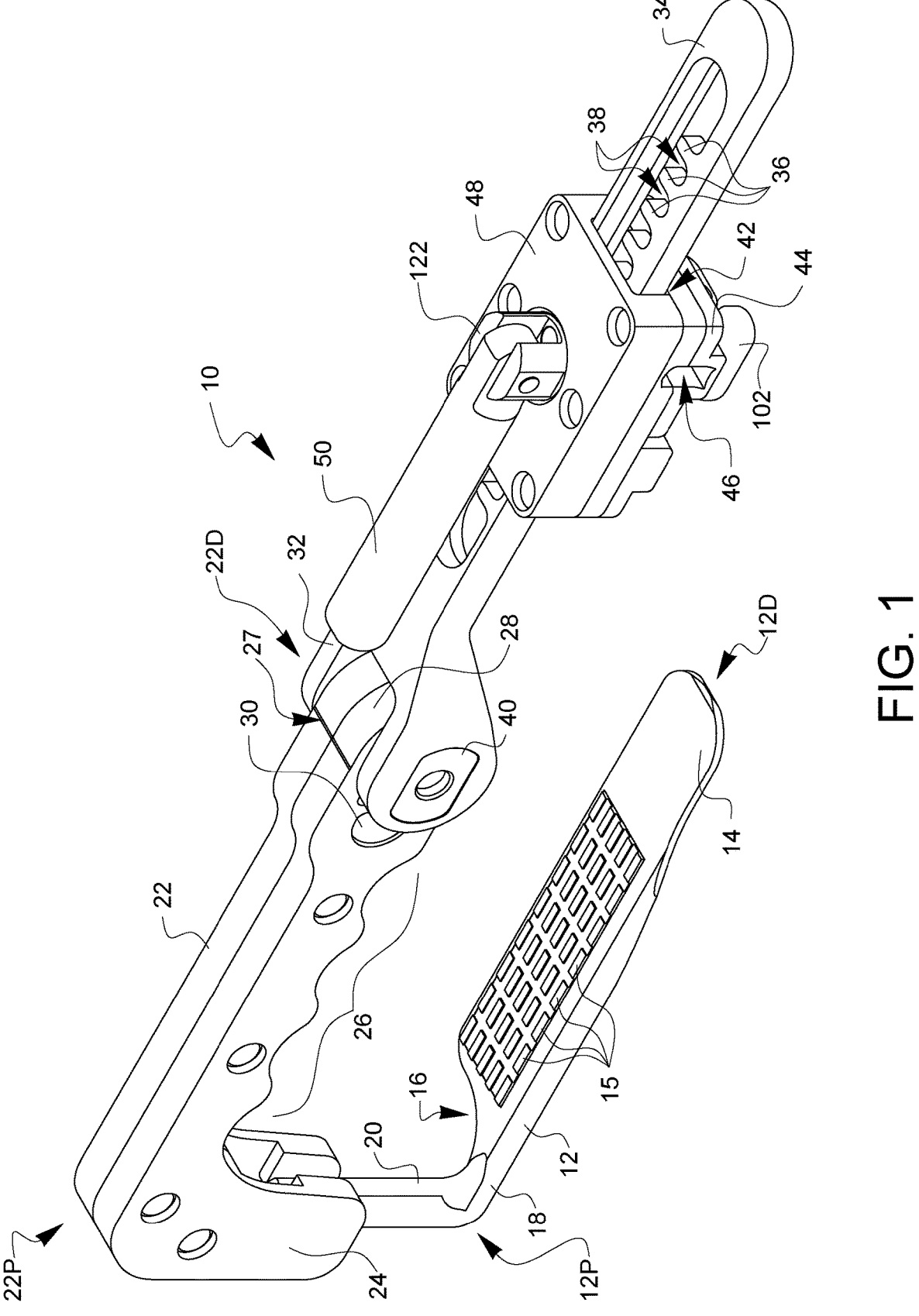
FIG. 1 is a top-front-right perspective view of one embodiment of a sternal ascender apparatus with a right sternal ascender attached.

It will be appreciated that for purposes of clarity and where deemed appropriate, reference numerals have been repeated in the figures to indicate corresponding features, and that the various elements in the drawings have not necessarily been drawn to scale in order to better show the features.

SUMMARY

A sternal ascender apparatus is disclosed. The sternal ascender may include a panel, a support beam traversing the panel, and a post coupled to a proximal end of the panel. The apparatus may also include an indicator handle coupled to the sternal ascender, an actuator drive pivotally coupled to the indicator handle, and a housing movably coupled to the actuator drive. The sternal ascender apparatus may have an actuator drive incorporating a linear rack. The housing further may include a cylindrical gear where the cylindrical gear is engaged with the linear rack.

Another sternal ascender apparatus is disclosed. The sternal ascender may include a panel having a plurality of textural features, a support beam traversing the panel, and a post coupled to a proximal end of the panel. The apparatus may also include an indicator handle removably coupled to the sternal ascender, an actuator drive pivotally coupled to the indicator handle having a linear rack, and a housing movably coupled to the actuator drive having a cylindrical gear and two instrument adapters.

DETAILED DESCRIPTION

FIG. 1 is a perspective view of one embodiment of a sternal ascender apparatus with a right sternal ascender attached. An embodiment of a sternal ascender apparatus 10 is shown in FIG. 1, with a right sternal ascender 12 installed therein. The right sternal ascender 12 defines a panel 14, the panel 14 having several textural features 15 configured to provide an atraumatic yet firm grip on the underside of a ribcage when the sternal ascender assembly 10 is in use in a minimally invasive surgical procedure. The panel 14 of the right sternal ascender 12 also defines a notch 16 and has a support beam 18 on the underside of the panel 14 The right sternal ascender 12 has a mounting post 20 on a proximal end 12P. The mounting post 20 is coupled to a proximal end 22P of an indicator handle 22 at the end of the mounting portion 24 of the indicator handle 22. The right sternal ascender 12 is coupled by reversible means such that the right sternal ascender 82 may be easily removed and replaced with a left sternal ascender, which is not shown in this view. The term ascender may be used interchangeably with the term elevator or lifter, as they equivalently describe the intended function of the ascender and associated apparatus. This coupling means will be described in further detail later. One alternate example of a coupling method is using a set screw, although others may be known to those skilled in the arts. The indicator handle 22 further defines a grip 26 in the underside of the indicator handle 22, which is configured for an ergonomic gripping feature for the comfort of use by a surgeon. At a distal end 22D of the indicator handle 22 is a connection end 28 and a pressable switch 30. Towards the distal end 22D of the indicator handle 22 is a depth indication mark 27, which is vertically aligned with the distal end 12D of the right sternal ascender 12. The connection end 28 is a coupling point that accepts a corresponding connection end 32 on a linear rack or linear actuator gear 34 by way of mating with the connection end 28 and is pivotably attached by joining a pivot pin 40 or alternatively by other attachment means into a hole or other attachment means not shown in this view. The pressable switch 30 can be pressed or actuated to defeat a pawl that is located inside the indicator handle 22, but not shown in this view. The pawl interfaces with a fixed indexing gear located inside the connection end 32 portion of the linear actuator gear 34. This will be discussed later in more detail in regard to FIGS. 2A-2E. The pawl defines a spring or biasing element to bias, while at rest, one or more teeth defined by the pawl toward the fixed indexing gear, which is not shown in this view but is coupled to the connection end 32 of the linear actuator gear 34. When the one or more teeth on the pawl intermesh with one or more corresponding teeth or other locking feature defined by the fixed indexing gear, this locks the angular position of the linear actuator gear 34 relative to the position of the indicator handle 22. When switch 30 is pressed or actuated, the pawl is defeated and temporarily pushed away from the fixed indexing gear, allowing free angular movement of the linear actuator gear 34 relative to the indicator handle 22. Releasing the switch 30, re-engages the pawl and the fixed indexing gear to once again interface and lock the angular position of the linear actuator gear 34 relative to the indicator handle 22 that it was in when the switch 30 was released.

The linear actuator gear 34 further defines several teeth 36 and several recesses 38 that engage a cylinder gear 122. The linear actuator gear 34 fits through an actuator slot 42 in a dual side instrument adapter 44. The dual side instrument adapter 44 defines a first adapter channel 46 and a second adapter channel, not visible here, on the opposite side. The dual side instrument adapter 44 also defines several locking mechanisms 100, 102 for locking the dual side instrument adapter 44 into a surgical equipment holder on each side. Once the dual side instrument adapter 44 is attached on each side to a surgical equipment holder, it can be positioned over a patient by bridging two surgical equipment holders across a surgical table. Other embodiments may only have a single adapter channel for mounting onto a single surgical equipment holder. Attached to the dual side instrument adapter 44 is a gear housing 48 which holds the cylinder gear 122. A handle or swivel bar 50 is coupled to the cylinder gear 122. Turning the handle 50 rotates the cylinder gear 122 and thereby moves the linear actuator gear 34 back and forth which forms an actuator drive. In this embodiment, the sternal ascender assembly 10 is inserted into an incision below the sub-xiphoid of a patient undergoing a minimally invasive surgical procedure, such as an ITA harvesting procedure or other surgical procedure in which increased access space below the sub-xyphoid process is advantageous. The panel 14 of the right sternal ascender 12 can be used to enable lifting the ribcage, thereby increasing space in the subxiphoid area. One feature of the sternal ascender assembly 10 is that the length of the distal end 22D of the indicator handle 22 is substantially the same as the length of the right sternal ascender 12 panel 14, which provides the surgeon with a visible indication, along with the depth indication mark 27 of how far the right sternal ascender 12 or the right sternal ascender (if installed into the sternal ascender apparatus 10) has been inserted into the subxiphoid cavity of the patient. The distal end 22D of the indicator handle 22 is substantially aligned with a distal end 12D of the sternal ascender 12. The indicator handle 22 is also substantially parallel to the panel 14 of the right sternal ascender 12 or the panel of a right sternal ascender. Once the sternal ascender apparatus or assembly 10 is inserted into the subxiphoid cavity, the sternal ascender assembly 10 is attached to one or more surgical equipment holders, enabling stability of force throughout a minimally invasive surgical procedure. Further adjustments to the position of the sternal ascender assembly 10 may then be made by pivoting about the coupling joint of the indicator handle 22 and the linear actuator gear 34. The sternal ascender assembly 10 can be further adjusted by rotating the swivel bar 50 and actuating the linear actuator gear 34 in a distal direction. This operation will be discussed in further detail later.

Figure 2A:
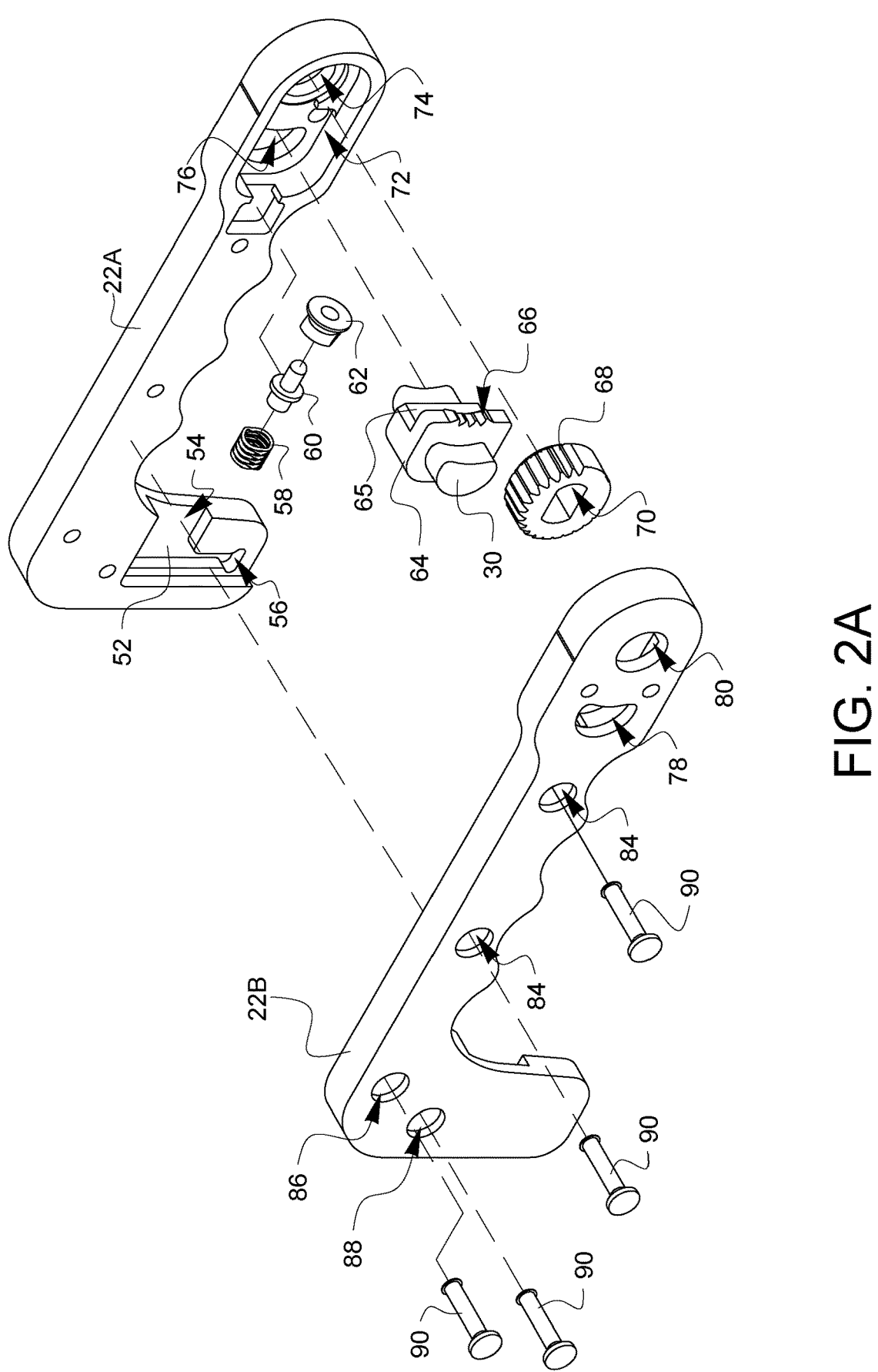
FIGS. 2A-2E is a series of exploded views illustrating the apparatus of the sternal ascender apparatus of FIG. 1.

FIGS. 2A-2E is a series of exploded views illustrating the assembly of the sternal ascender apparatus of FIG. 1. As illustrated in FIG. 2A, a first handle half 22A defines a recess or channel 52 having a mounting slot 54 and a seat 56. The mounting slot 54 and seat 56 defined by the channel 52, also referred to as a t-slot based on the general shape thereof, is configured to removably receive an alignment key on the post of either a left or right sternal ascender. A second handle half 22B also defines a corresponding recess, not shown in this view. The first handle half 22A also defines a second recess 72 at an opposite end and a gear recess 74 and hole 76. The second handle half 22B also defines a corresponding recess, not shown in this view. The second recess 72 is configured to receive and hold a spring 58, spring plunger 60, and plunger housing 62, which are first assembled together. A pawl gear 64 having gears 66 and an ungeared portion 65 and a fixed indexing gear or a pivot gear 68 having a gear keyway 70 are placed into hole 76 and held in gear recess 74, respectively, on the first handle half 22A. The pawl gear 64 is held against the spring 58, spring plunger 60, and plunger housing 62 assembly such that the pawl gear 64 is biased against the pivot gear 68 until the pawl gear 64 is depressed to slide the pawl gear 64 so that the gears 66 are disengaged from the pivot gear 68 such that it interfaces with the ungeared portion 65 of the pawl gear 64, thus allowing free rotation or pivoting of the pivot gear 68. When the pawl gear 64 is released, the gears 66 relock with the pivot gear 68 preventing further pivoting or rotation of the pivot gear 68. The second handle half 22B is then placed over the first handle half 22A and fastened using several rivets 90 which are placed and fixed into holes 84, 86, 88 on the second handle half 22B. While holes and rivets are used here to fixedly attach the handle halves 22A, 22B together, welding, adhesives or other means known to those skilled in the art may also be employed.

Figure 2B:
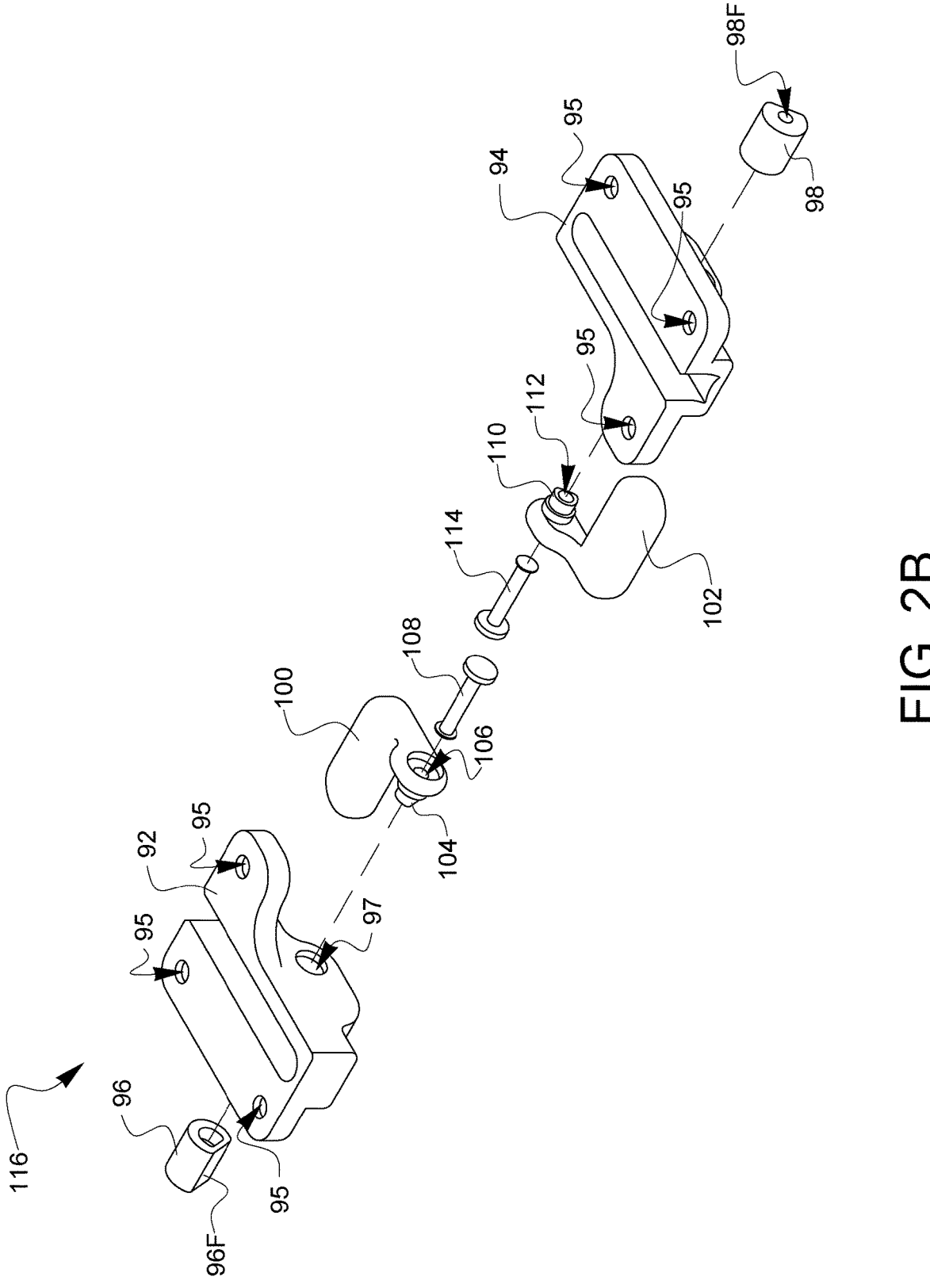

FIG. 2B illustrates the assembly of an instrument adapter assembly 116 portion of the sternal ascender apparatus 10. A first adapter housing 92 having several holes 95 and side hole 97 is assembled by placing a first cam 96 having a flat 96F into hole 97. A first lever lock 100 having a key 104 is placed into hole 97 and into the first cam 96 such that rotating the first lever lock 100 will also rotate the first cam 96 within hole 97. The first lever lock 100 is pivotably attached to the first adapter housing 92 with the use of rivet 108 being placed into channel 106 on the first lever lock 100. A second adapter housing 94 having several holes 95 and side hole, not visible here, is assembled by placing a second cam 98 having a flat 98F into hole 97. A second lever lock 102 having a key 110 is placed into a hole on the second adapter housing 94 and into the second cam 98 such that rotating the second lever lock 102 will also rotate the second cam 98 within the hole in the second adapter housing 94. The second lever lock 102 is pivotably attached to the second adapter housing 94 with the use of rivet 114 being placed into channel 112 on the second lever lock 102.

Figure 2C:
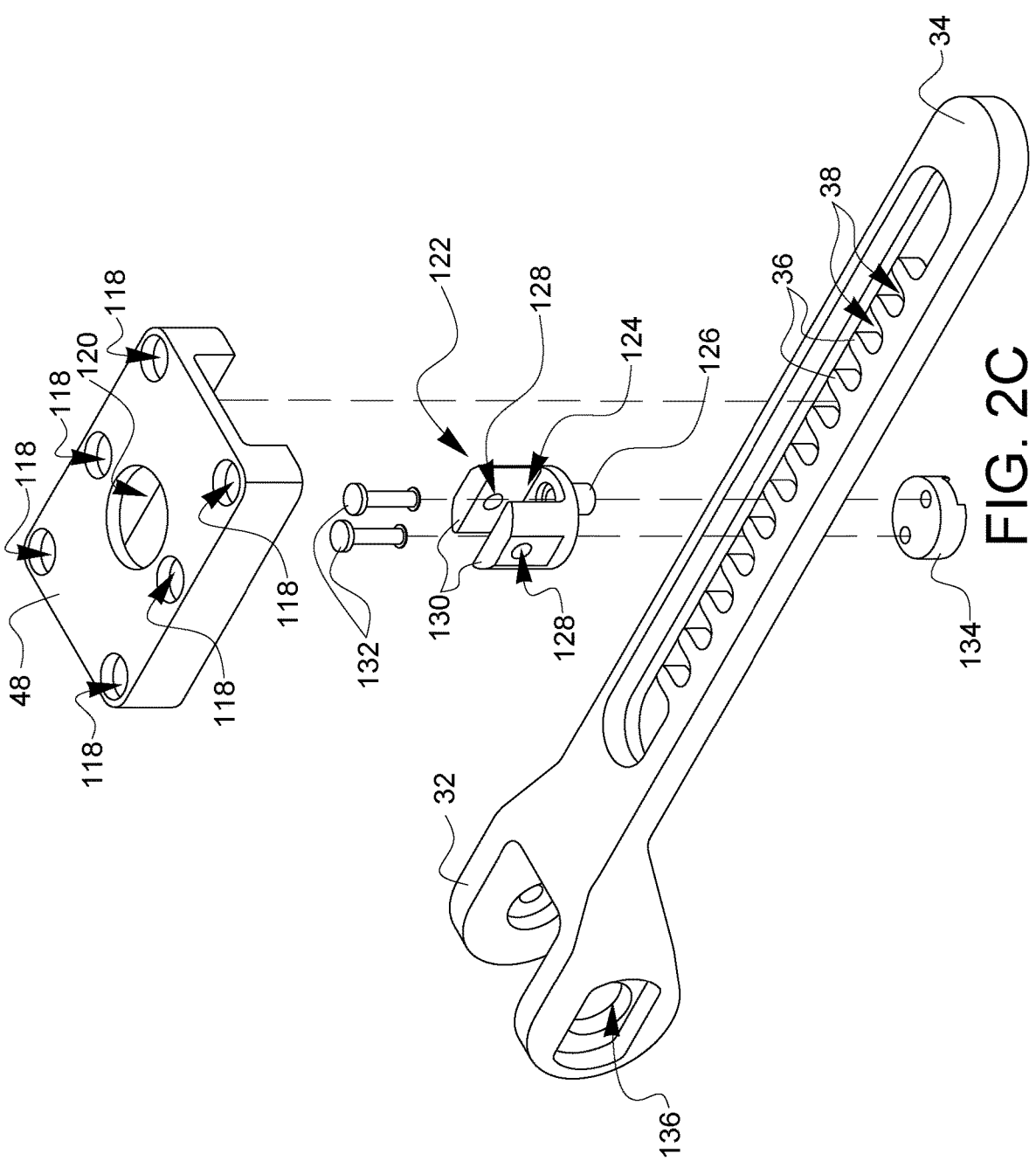
Figure 2D:
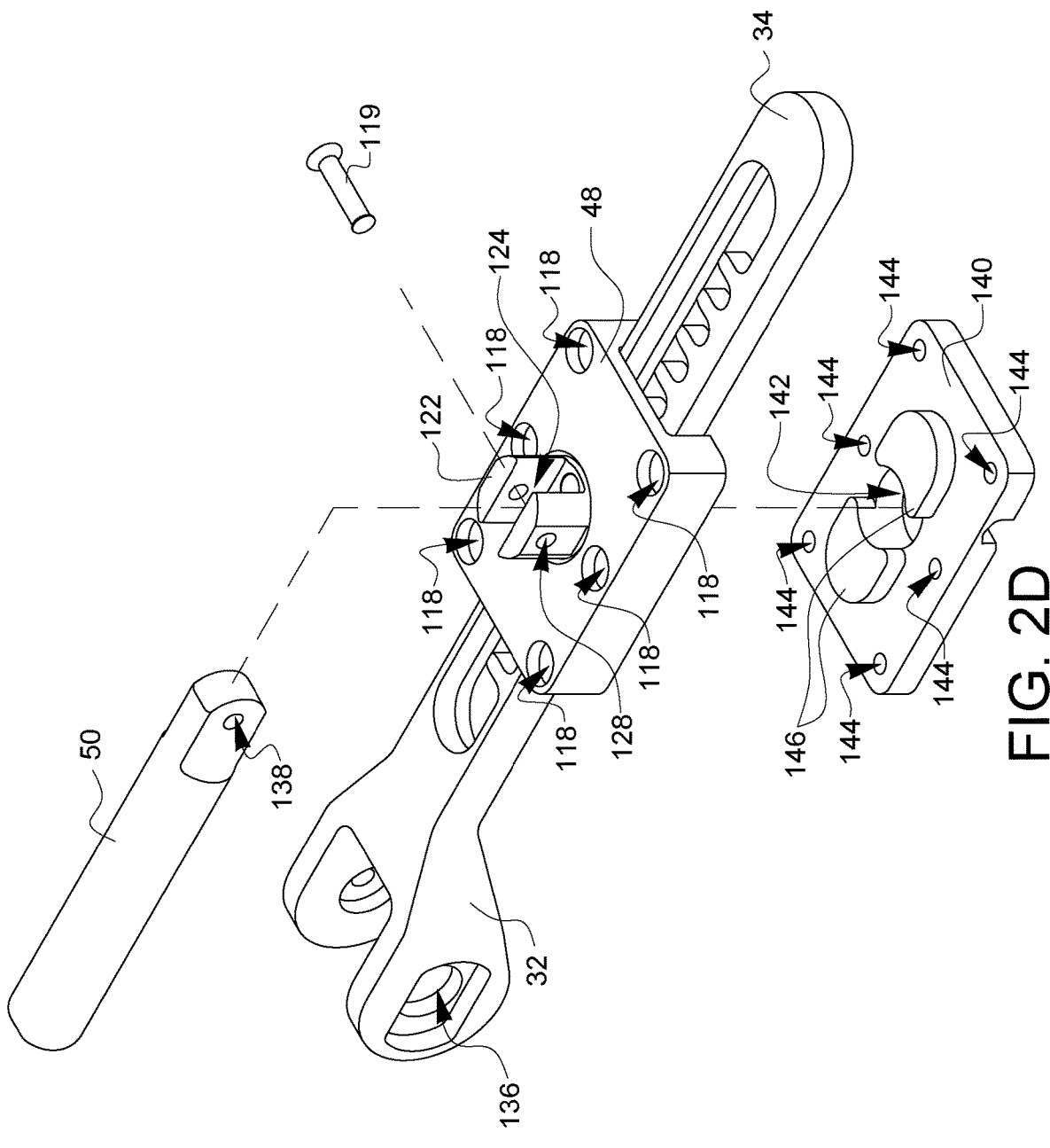
Figure 2E:
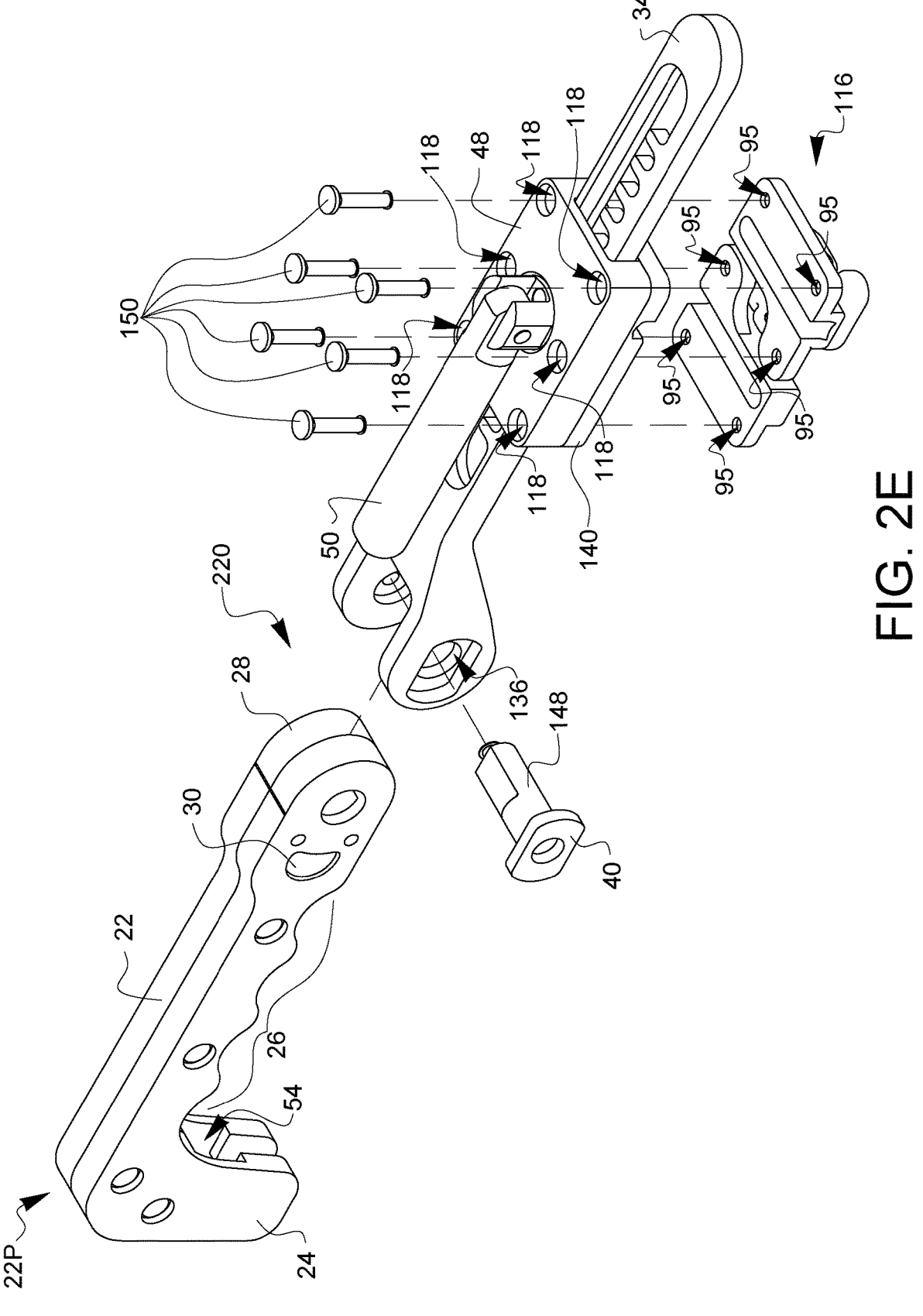

FIG. 2C continues the assembly of the sternal ascender apparatus 10 focusing on the linear actuator gear 34. The linear actuator gear 34, having a connection end 32 which further defines a hole 136 and several teeth 36 with several recesses 38 positioned therebetween. A cylinder gear 122 defines two sides 130, a side channel 128 on either side 130, a slot 124, and two posts 126, one of which is visible here, is placed into the linear actuator gear 34 with the two posts 126 held in two adjacent recesses 38. A drive bottom 134 is fixed with two rivets 132 onto the two posts 126 of the cylinder gear 122 on the opposite side of the linear actuator gear 34. Once fully assembled, the cylinder gear 122 is rotated in a clockwise or counterclockwise direction this thereby moves the linear actuator gear back and forth forming an actuator drive. As the cylinder gear 122 is rotated, the first pinion or post 126 will rotate out of a recess 38 on the linear actuator gear 34 and outward while the second pin driver (not visible here) remains in a second recess 38 and rotates within the second recess 38. The first post 126 will rotate into a third recess 38, past the second recess 38 thus translating rotational motion into linear motion and moving the linear actuator gear 34 relative to the gear housing 48. Performing this operation in the reverse will move the actuator gear 34 in the reverse direction. A upper rack housing 48 having a central opening 120 and several holes 118 is then placed over the linear actuator gear 34 and cylinder gear 122 so that the cylinder gear 122 protrudes from the central opening 120 of the upper rack housing 48 and the upper rack housing 48 is able to slide along the linear actuator gear 34 as the cylinder gear 122 is rotated. FIG. 2D illustrates the handle 50 being placed into the cylinder gear 122 between the two sides 130 and held in place by placing a rivet 119 through the side channels 128 on the cylinder gear 122 and through the hole 138 on the swivel bar 50. A middle rack housing 140 having a central hole 142, several holes 144, and two housing inserts 146 is placed onto the bottom of the linear actuator gear 34 to align with the upper rack housing 48. The holes 118 on the upper rack housing 48 are aligned with the holes 144 on the middle rack housing 140. The two housing inserts 146 are configured to hold captive and allow free rotation of the drive bottom 134 of the cylinder gear 122. The handle or swivel bar 50 is used to swivel and rotate the cylinder gear 122 during operation. The assembly of the sternal ascender apparatus 10 is completed in FIG. 2E by inserting the distal end 22D of the indicator handle 22 into the linear actuator gear 34. The pivot pin 40 is inserted into hole 136 with the pivot pin post 148 interlocking into the gear keyway 70 of the pivot gear 68, the function of which was illustrated in FIG. 2A. The instrument adapter assembly 116 shown and described in regard to FIG. 2B is placed onto the bottom of the middle rack housing 140 and holes 95 in the instrument adapter assembly 116 are aligned with the corresponding 118 holes in the upper rack housing 48. Several rivets 150 are then placed into the holes 118 to fixedly join the instrument adapter assembly 116 to the middle rack housing 140 and upper rack housing 48.

Figure 3:
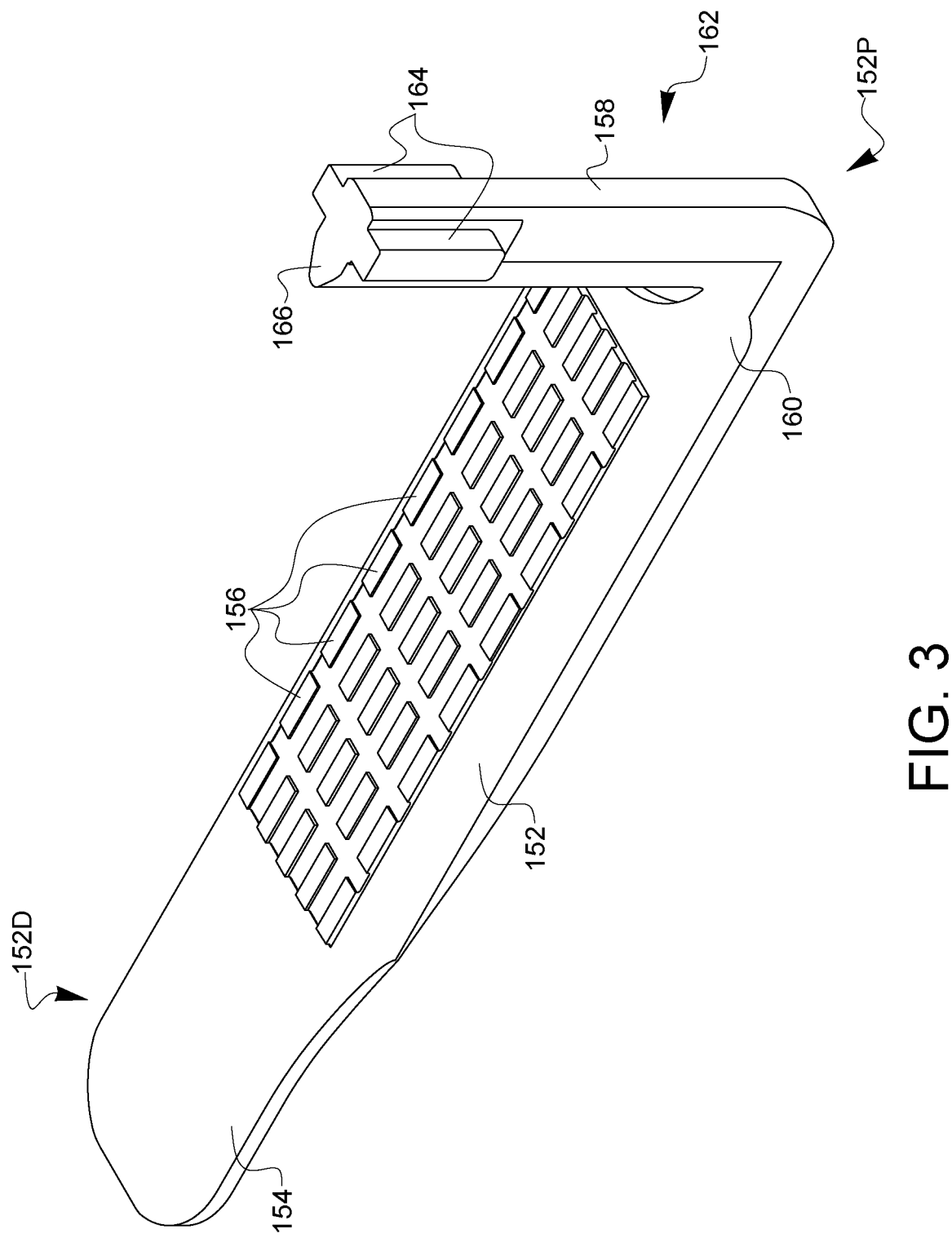
FIG. 3 is a perspective view of a left sternal ascender.
Figures 4A, 4B, 4C, 4D, 4E, 4F:
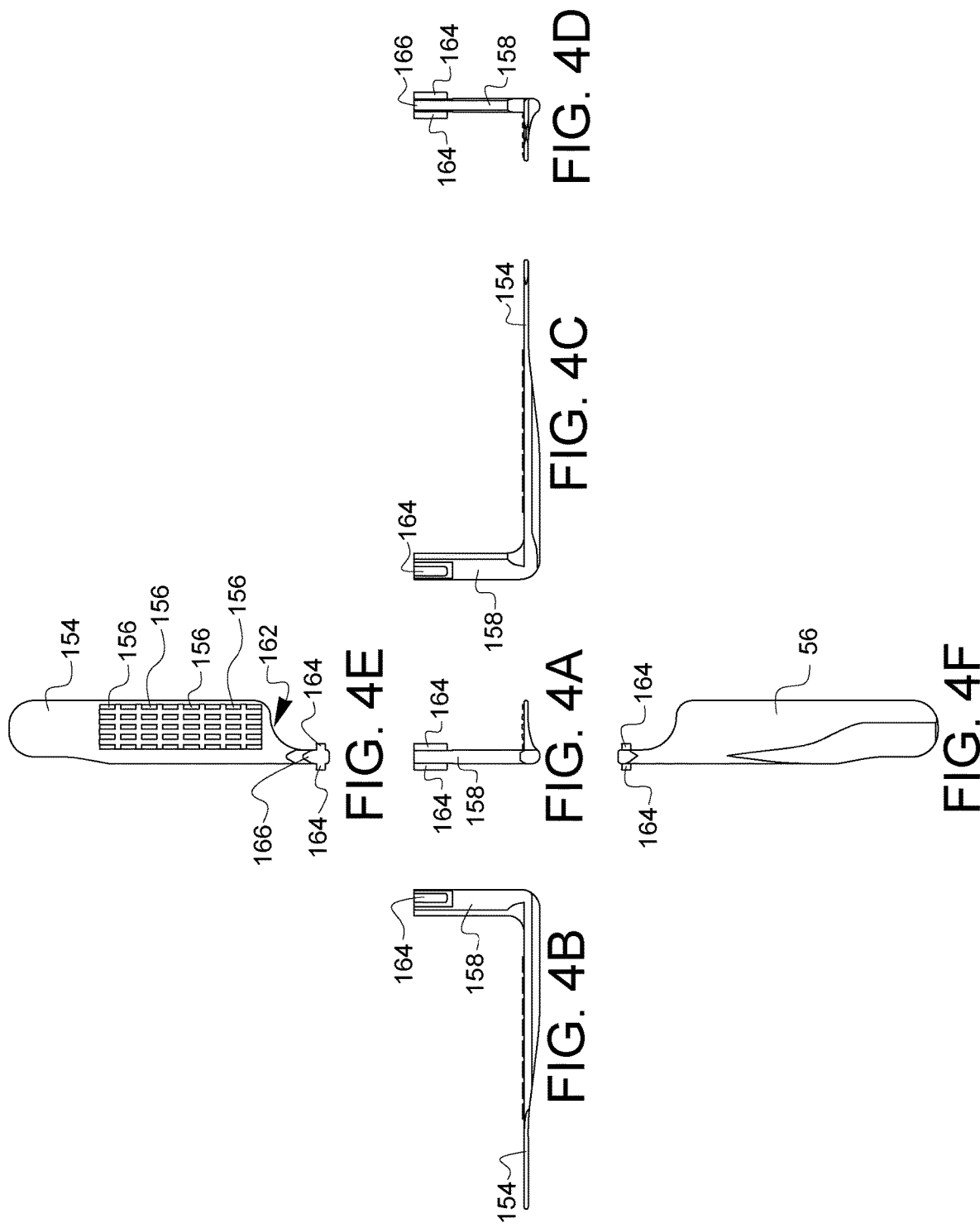
FIGS. 4A, 4B, 4C, 4D, 4E, and 4F are front, left side, right side, rear, top, and bottom elevational views, respectively, of the sternal ascender of FIG. 3.

FIG. 3 is a perspective view of a left sternal ascender. This view illustrates the various features defined by the left sternal ascender 152. The left sternal ascender 152 defines a panel 154 having several textural features 156, a contralateral, or pertaining to the opposite side of targeted anatomical area, notch 162 at a proximal end 152P, a support beam 160 traversing the underside of the panel 154, and a mounting post 158 for attachment to a sternal ascender apparatus 10. The panel 154 has a rounded shape with a slight edge at a distal end 152D of the panel 154 of the left sternal ascender 152. Also defined by the post 158 are two opposing alignment and orientation features 164 configured to align, slide and lock the left sternal ascender 152 into the handle. These features 164 form a general t-shape, which are configured to fit into the aforementioned t-slot on the indicator handle 22. The use of this feature will be described further in regard to FIGS. 7A-7C. The post 158 also defines an angular front alignment feature 166 which is used to help align and place the left sternal ascender in an anatomical notch defined between a rib and sternum. This can serve as a tactile assist in placing the sternal ascender in an appropriate place when in use as part of a sternal ascender apparatus. While the embodiment shown has these characteristics, alternate embodiments of a sternal ascender panel may have other shapes or radiuses, and may or may not be sharpened. Still other embodiments may have other features aside from the rectangular textural features 156 shown here, and may include other shaped features or none at all. Other embodiments of left sternal ascenders may be made of metal, plastic, composites, or mixtures or combinations thereof or contain alternate alignment or locking methods and features. FIGS. 4A, 4B, 4C, 4D, 4E, and 4F are front, left side, right side, rear, top, and bottom elevational views, respectively, of the sternal ascender of FIG. 3.

Figure 5:
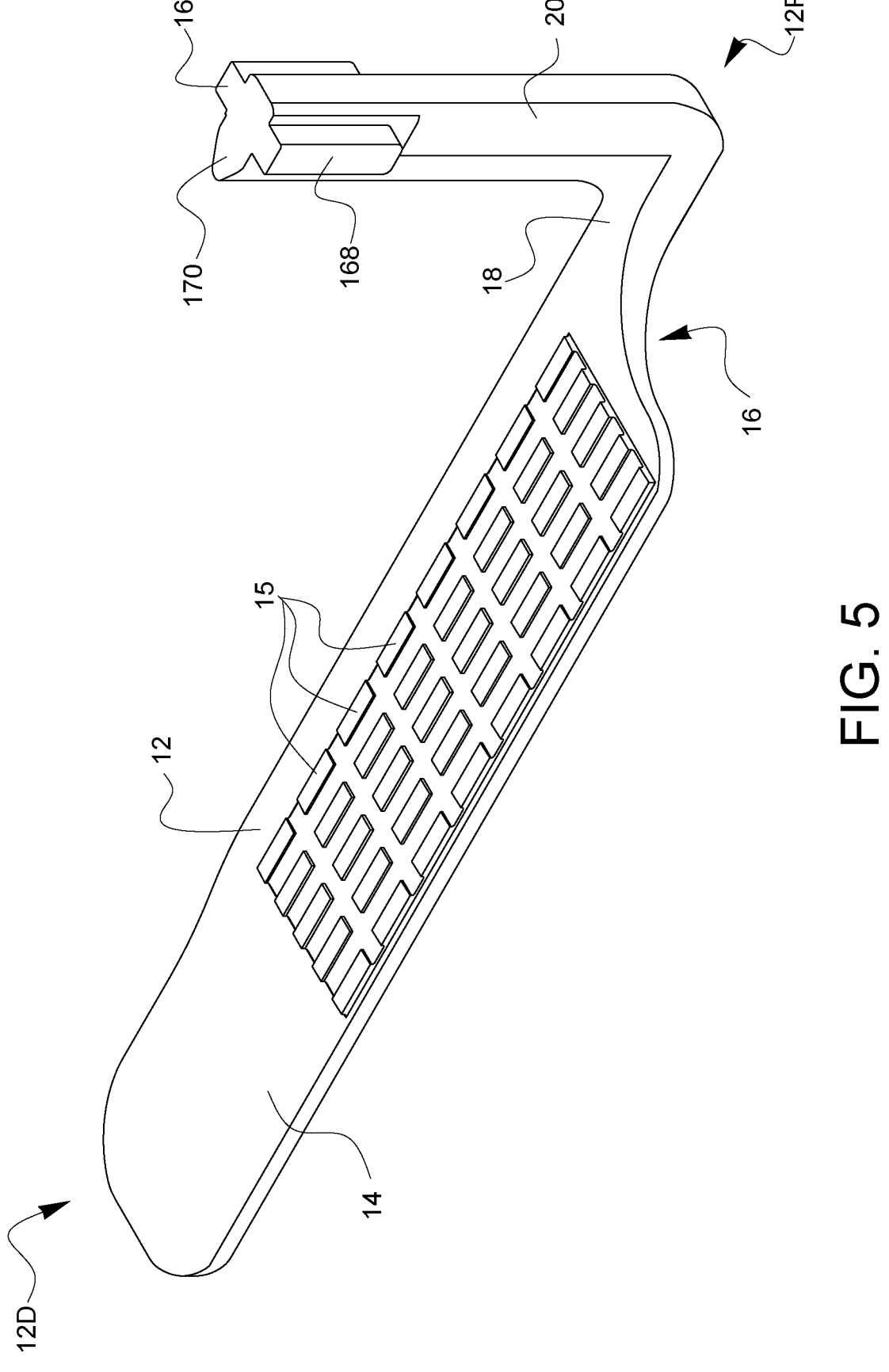
FIG. 5 is a perspective view of a right sternal ascender.
Figures 6A, 6B, 6C, 6D, 6E, 6F:
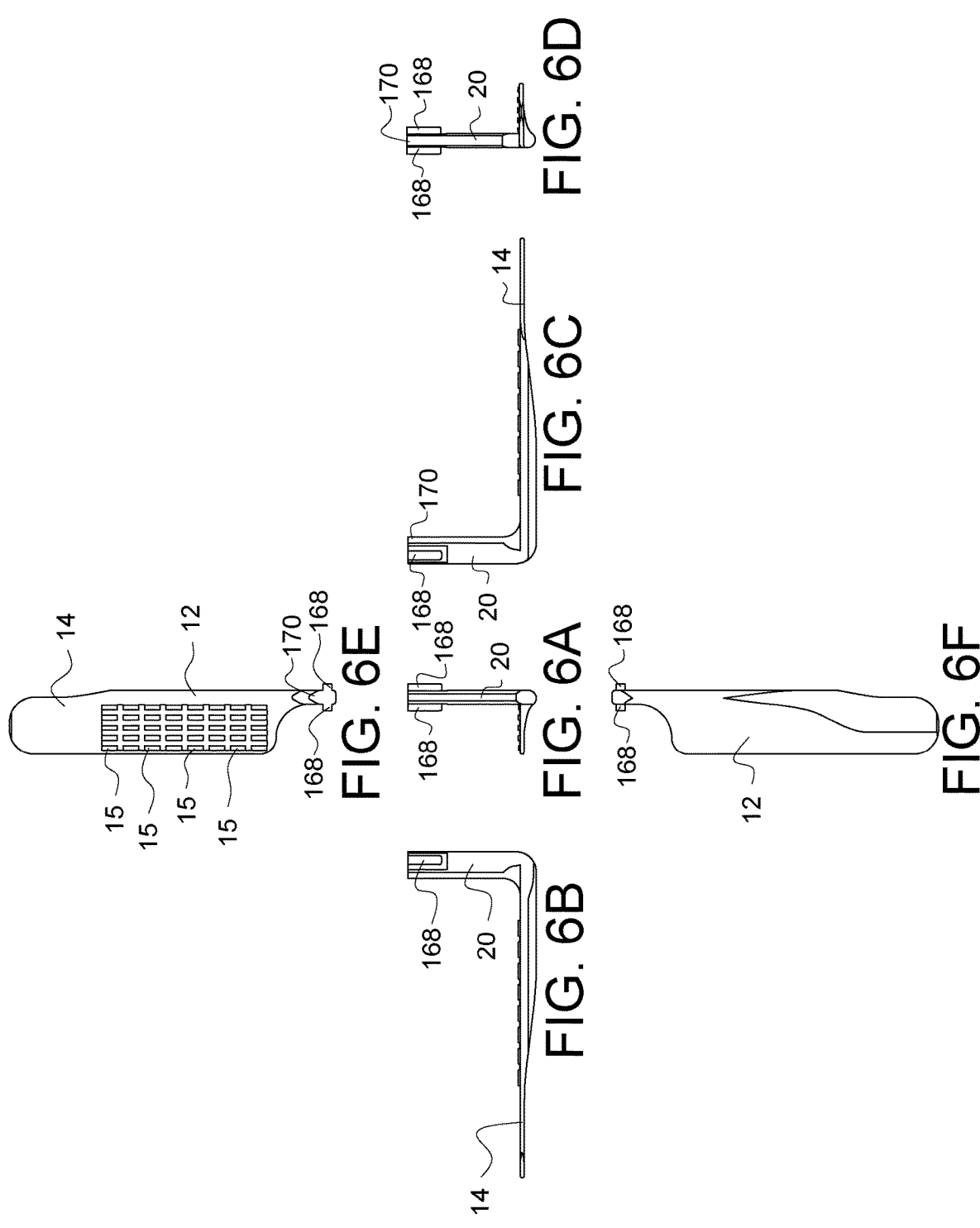
FIGS. 6A, 6B, 6C, 6D, 6E, and 6F are front, left side, right side, rear, top, and bottom elevational views, respectively, of the right sternal ascender of FIG. 5.

FIG. 5 is a perspective view of a right sternal ascender. This view illustrates the various features defined by the right sternal ascender 12. The right sternal ascender 12 defines a panel 14 having several textural features 15, a contralateral, or pertaining to the opposite side of targeted anatomical area, notch 16 at a proximal end 12P, a support beam, not shown here, traversing the underside of the panel 14, and a mounting post 20 for attachment to a sternal ascender assembly. The panel 14 has a rounded shape with a slight edge at a distal end 12D of the panel 14 of the right sternal ascender 12. Also defined by the post 20 are two opposing alignment and orientation features 168 configured to align, slide and lock the left sternal ascender 12 into the handle. These features 168 form a general t-shape, which are configured to fit into the aforementioned t-slot on the indicator handle 22. The use of this feature will be described further in regard to FIGS. 7A-7C. The post 20 also defines an angular front alignment feature 170 which is used to help align and place the left sternal ascender in an anatomical notch defined between a rib and sternum. This can serve as a tactile assist in placing the sternal ascender in an appropriate place when in use as part of a sternal ascender apparatus. While the embodiment shown has these characteristics, alternate embodiments may have other shapes or radiuses, and may or may not be sharpened. Still other embodiments may have other attachment features aside from the rectangular textural features 15 shown here, and may include other shaped features or none at all. Other embodiments of right sternal ascenders may be made of metal, plastic, composites, or mixtures or combinations thereof. FIGS. 6A, 6B, 6C, 6D, 6E, and 6F are front, left side, right side, rear, top, and bottom elevational views, respectively, of the right sternal ascender of FIG. 5.

Figure 10A:
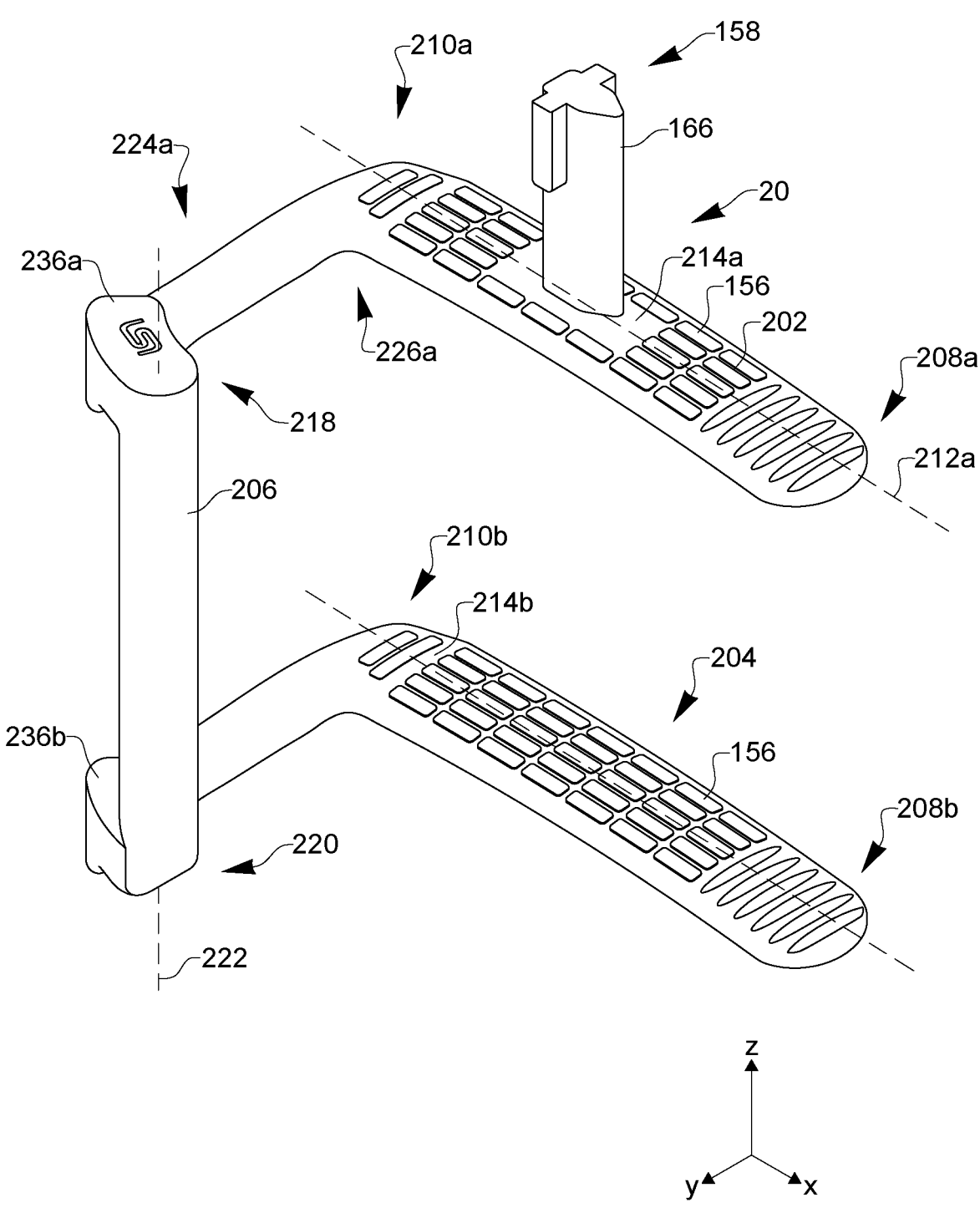
FIG. 10A is a first perspective view of an embodiment of a dual panel assembly that is configured to be coupled to the sternal ascender apparatus.

FIGS. 10A to 10H are various views of an embodiment of a dual panel assembly 200 that is configured to be coupled to the sternal ascender apparatus 10. FIG. 10A illustrates a perspective view of the dual panel assembly 200, which includes a top panel 202, and bottom panel 204, and a support column 206.

Figure 10B:
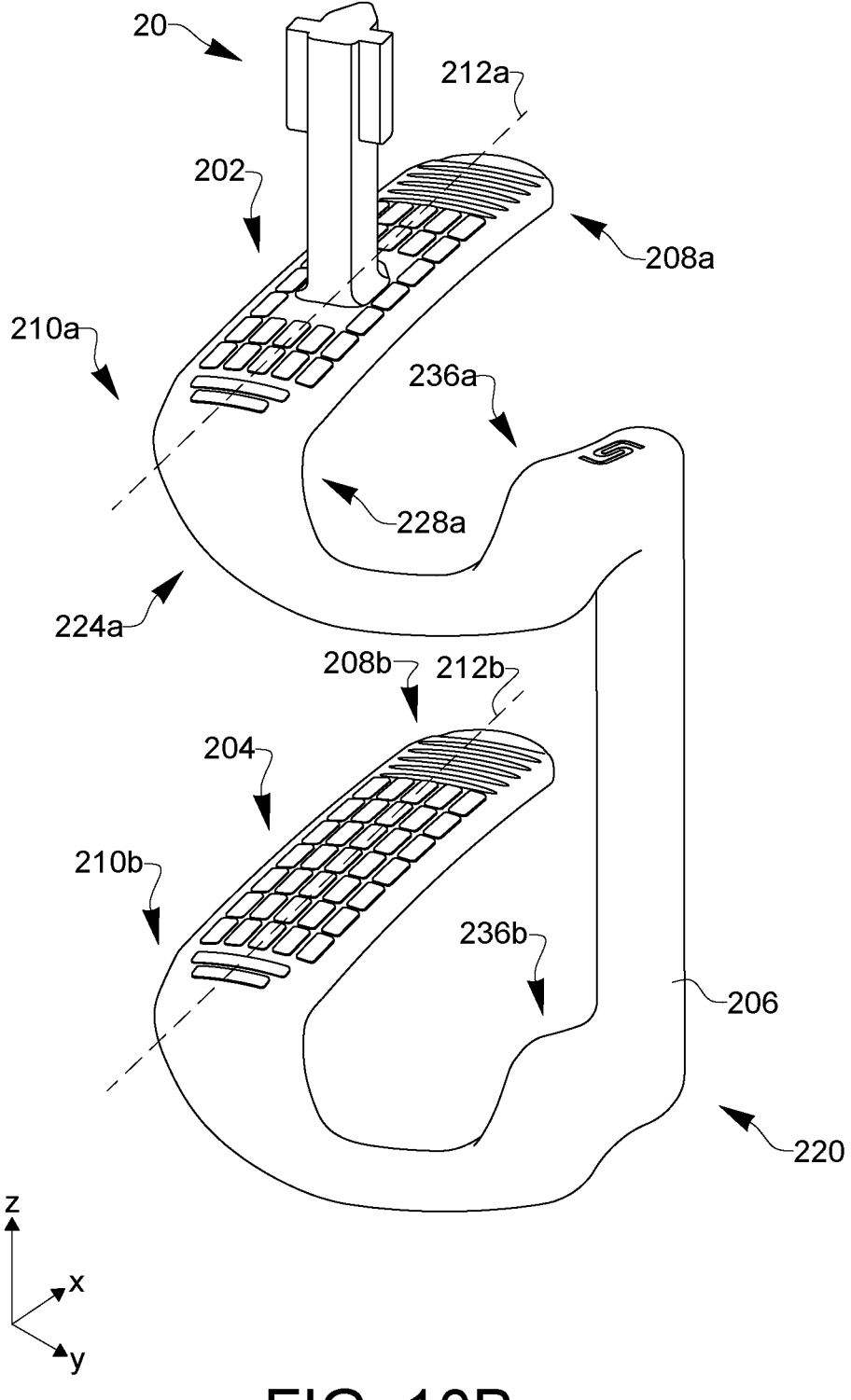
FIG. 10B is a second perspective view of the embodiment of the dual panel assembly of FIG. 10A.

With reference to the perspective views of FIGS. 10A and 10B, the top panel 202 may extend from a distal end 208a to a proximal end 210a along a longitudinal axis 212a that extends generally parallel to the X-axis of the reference coordinate system of FIG. 10A. The top panel 202 may be partially defined by an upper surface 214a that extends from the distal end 208a to the proximal end 210a of the top panel 202 along the longitudinal axis 212a. In some embodiments, may be partially defined by an upper surface 214a that extends from the distal end 208a to the proximal end 210a of the top panel 202 along the longitudinal axis 212a. However, as illustrated in the left side view of FIG. 10E, the upper surface 214b, or a distal portion of the upper surface 214b, may have a cambered shape or the shape of an arc or segment of a circle when viewed along the Y-axis of the reference coordinate system of FIG. 10E (also, illustrated in the cross-section of the identical bottom panel 204 in FIG. 10I). In some embodiments, a reference line 215a parallel to the X-axis of the reference coordinate system of FIG. 10A (that may also be parallel to the longitudinal axis 212a) may be tangent or approximately tangent to the upper surface 214a at or adjacent to the proximal end 208a. A plurality of textural features 156 may disposed over some or all of the upper surface 214a. In addition, the mounting post 20, 158 may extend from a portion of the upper surface 214a, and the mounting post 20, 158 may be similar or identical to the mounting post 20, 158 previously described. The mounting post 20, 158 may extend from a portion of the upper surface 214a along a longitudinal axis 217a that may be parallel to the Z-axis of the reference coordinate system of FIG. 10A. In some embodiments, the longitudinal axis 217a that may not be parallel to (e.g., may form an angle between 2° and 15° with) the Z-axis of the reference coordinate system of FIG. 10A.

The top panel 202 may also be partially defined by a lower surface 216a that is opposite to the upper surface 214a, and the lower surface 216a may extend from the distal end 208a to the proximal end 210a of the top panel 202 along the longitudinal axis 212a. In embodiment in which the upper surface 214a may be planar, the lower surface 216a may also be planar and, for example, may extend along a plane parallel to the X-Y plane of the reference coordinate system of FIG. 10A. However, as illustrated in the left side view of FIG. 10E, the lower surface 216a may have the same or similar arc or cambered shape as the upper surface 214a such that the top panel 202 has a uniform or substantially uniform cross sectional shape (when viewed along the longitudinal axis 212a) from a point at or adjacent to the distal end 208 to a point at or adjacent to the proximal end 210a, as illustrated in a first cross-sectional view of FIG. 10K and a second cross-sectional view of FIG. 10L. In some embodiments, the lower surface 216a may be slightly angled such that in cross-section, when viewed along the parallel to the longitudinal axis 212a as in FIGS. 10K and 10L, the lower surface 216a is disposed at an acute angle to the Y-axis of the reference coordinate system of FIGS. 10A, 10K, and 10L.

Referring to FIG. 10A, the dual panel assembly 200 also includes the support column 206 which is elongated and extends from a top end 218 to a bottom end 220 along a column axis 222 that extends parallel or substantially parallel to the Z-axis of the reference coordinate system of FIG. 10A. However, in some embodiments, the column axis 222 may extend at an acute angle relative to the Z-axis of the reference coordinate system of FIG. 10A, and in other embodiments, the column axis 222 may be non-linear. When viewed along an axis parallel to the Y-axis of the reference coordinate system of FIG. 10A and that intersects the longitudinal axis 212a of the top panel 202, the top end 220 of the support column 206 may be aligned with a portion of the top panel 202 at or adjacent to the proximal end 210a of the top panel 202 (e.g., a portion of the upper surface 214a that is at or adjacent to the proximal end 210a of the top panel 202). However, in other embodiments, the top end 220 of the support column 206 may extend beyond the portion of the top panel 202 at or adjacent to the proximal end 210a of the top panel 202. The support column 206 may have a cylindrical shape having a circular-cross-section, and height of the support column 206 may be between 5 to 20 times greater than the diameter of the cross-sectional circle. However, the support column 206 may have any suitable cross-sectional shape.

Figure 10C:
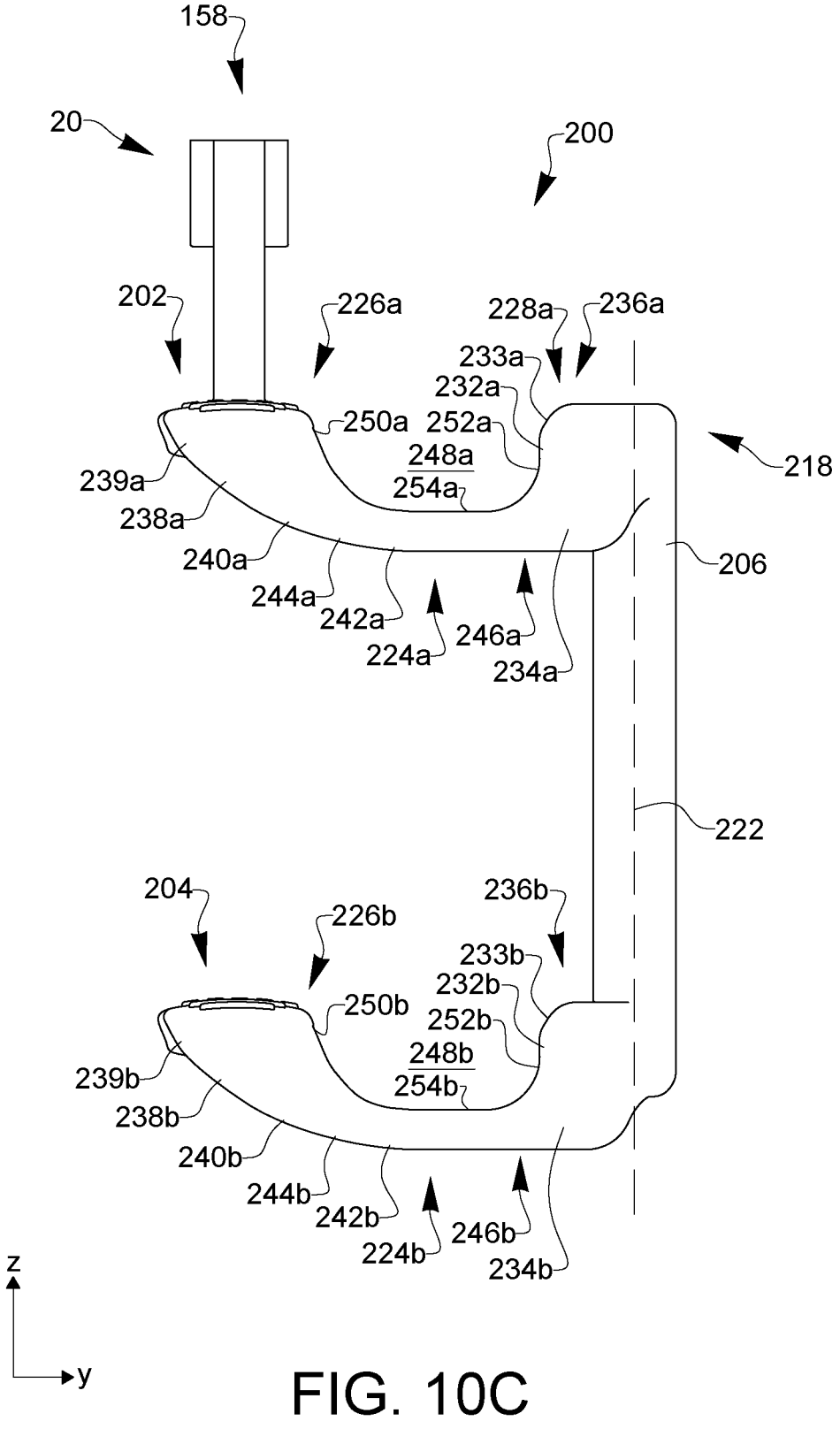
FIG. 10C is a rear view of the embodiment of the dual panel assembly of FIG. 10A.
Figure 10D:
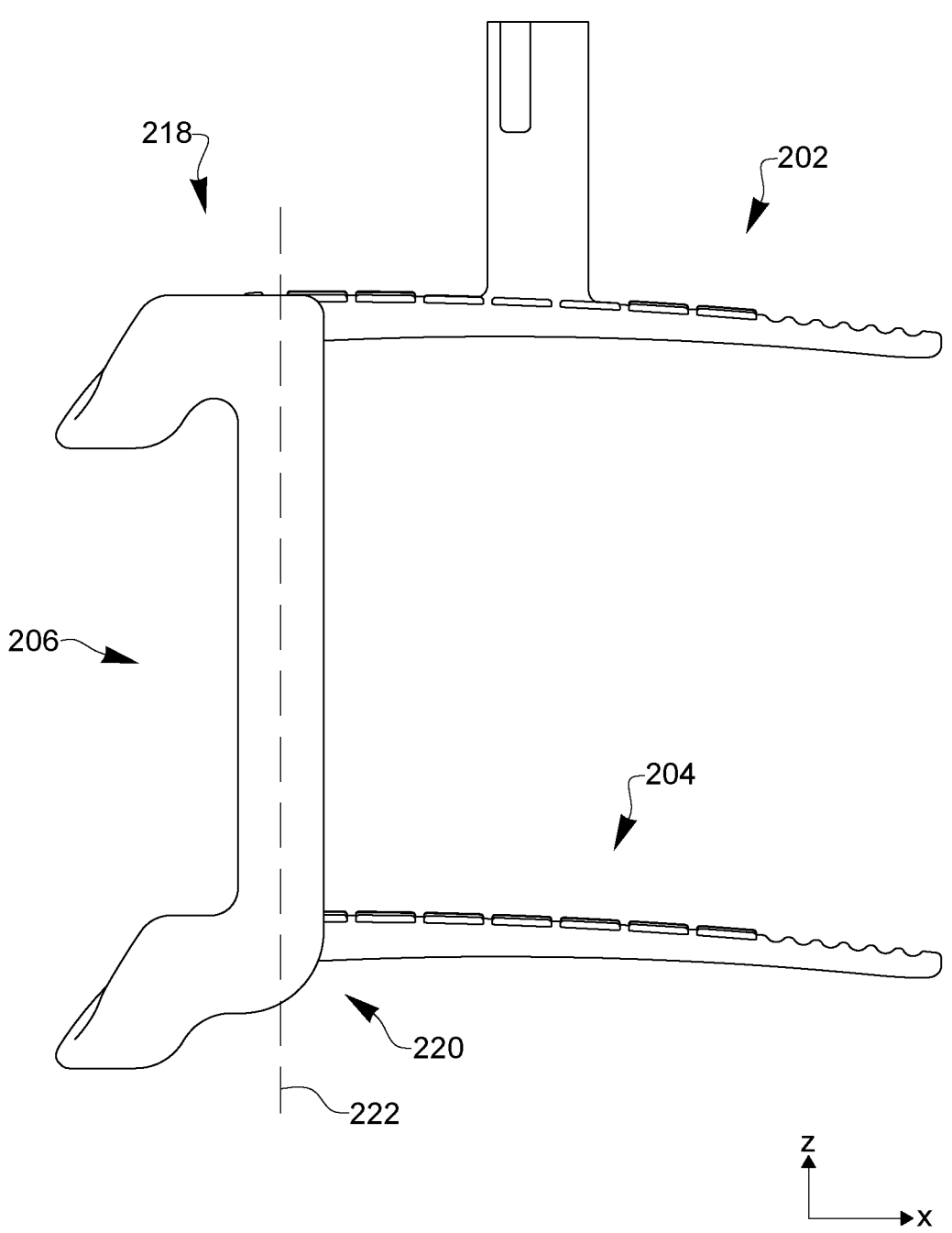
FIG. 10D is a first side view of the embodiment of the dual panel assembly of FIG. 10A.
Figure 10E:
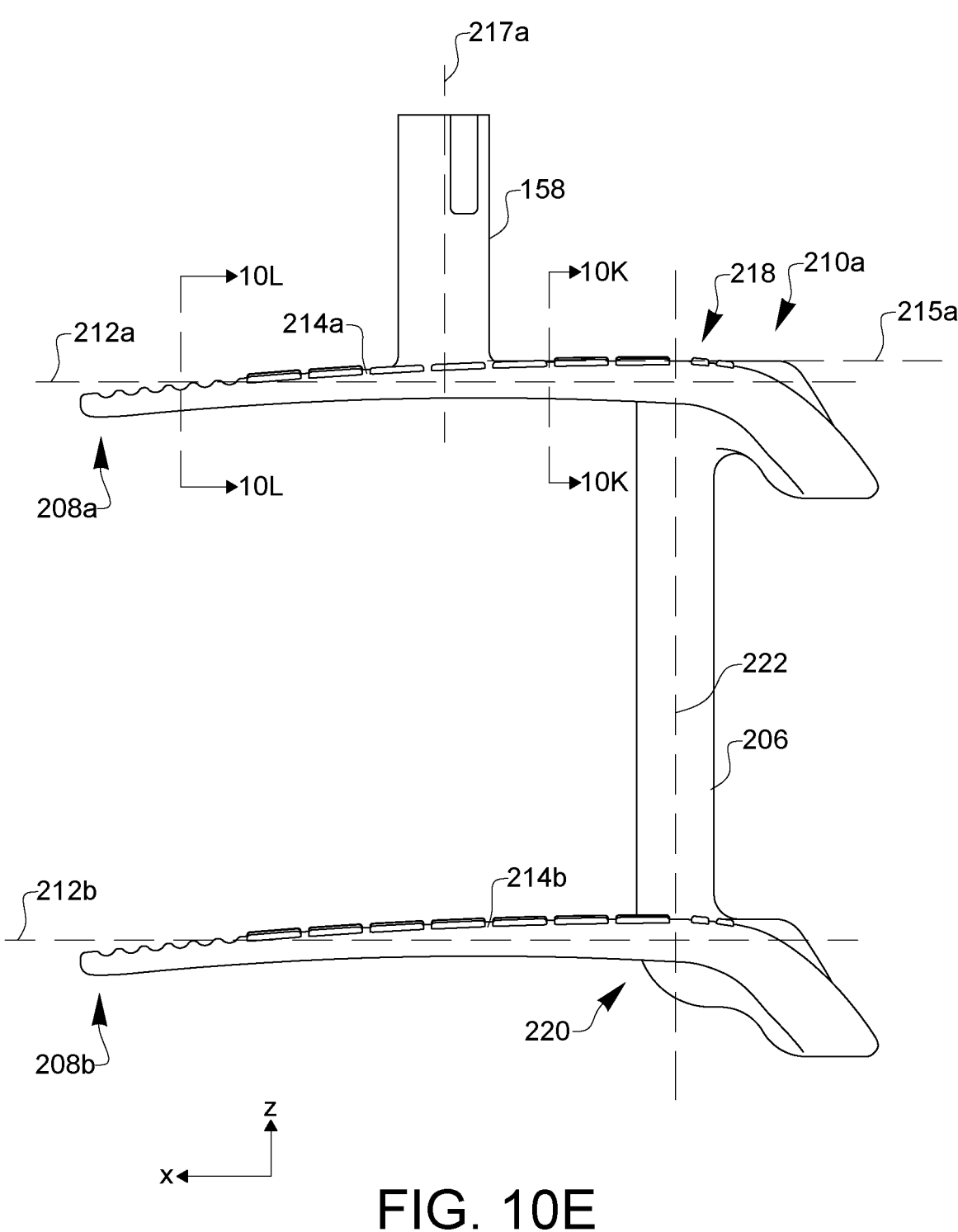
FIG. 10E is a second side view of the embodiment of the dual panel assembly of FIG. 10A.
Figure 10F:
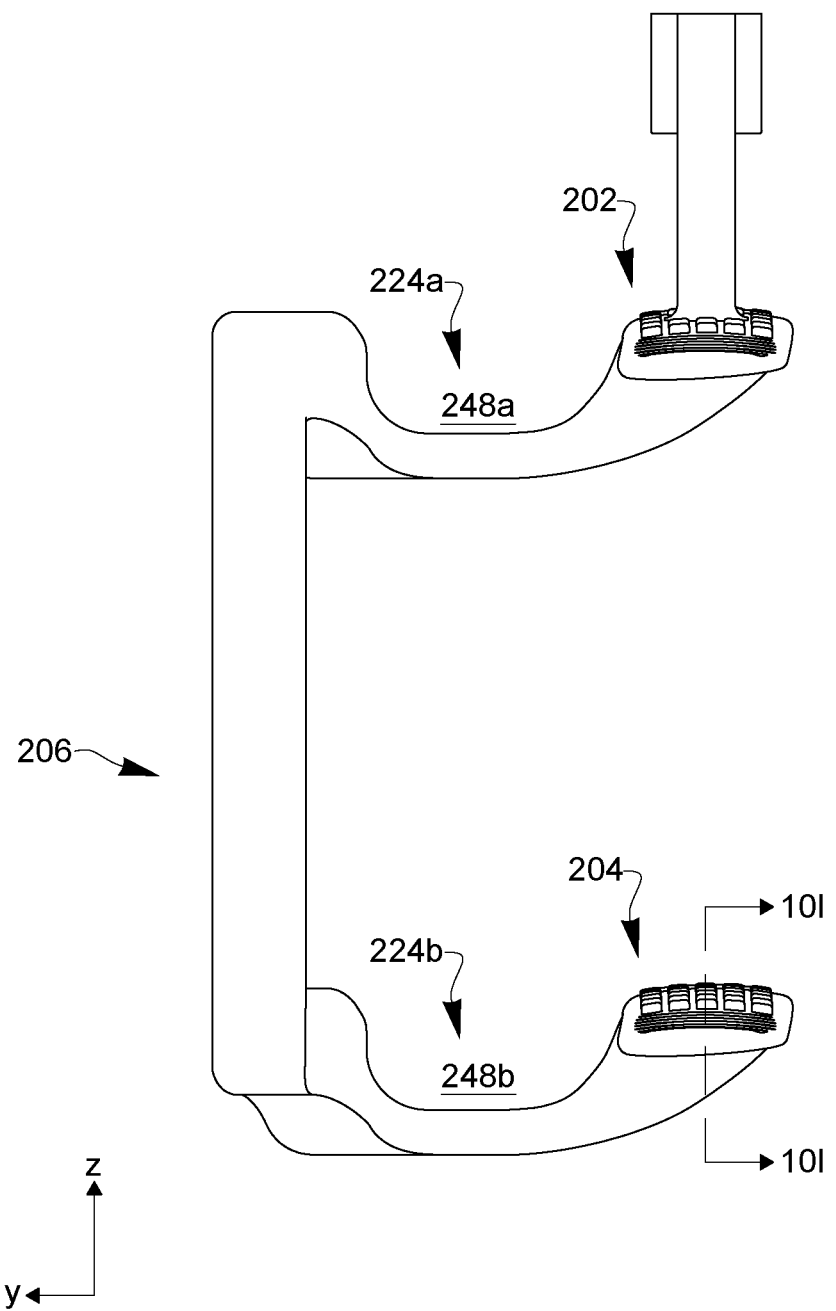
FIG. 10F is a front view of the embodiment of the dual panel assembly of FIG. 10A.
Figure 10G:
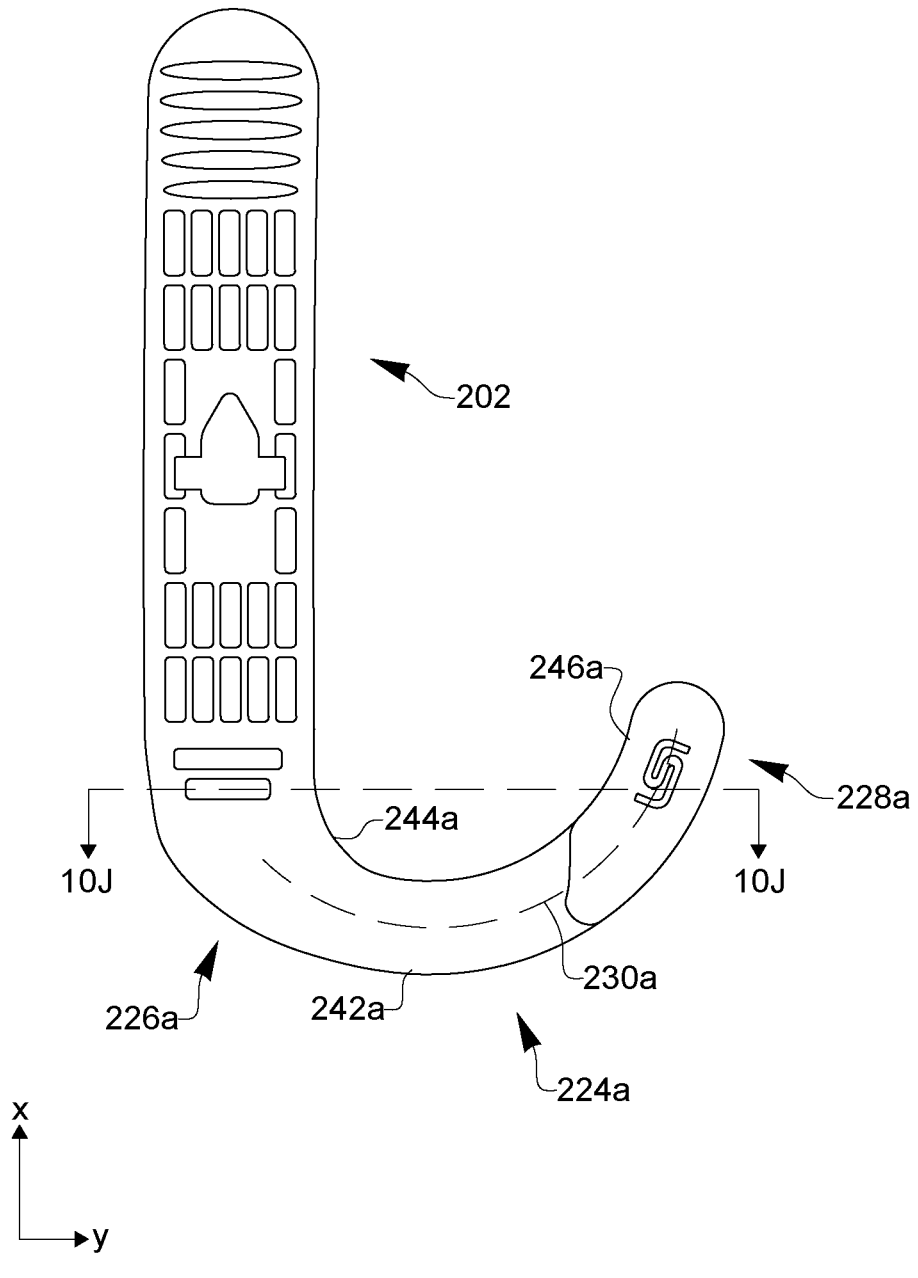
FIG. 10G is a top view of the embodiment of the dual panel assembly of FIG. 10A.
Figure 10H:
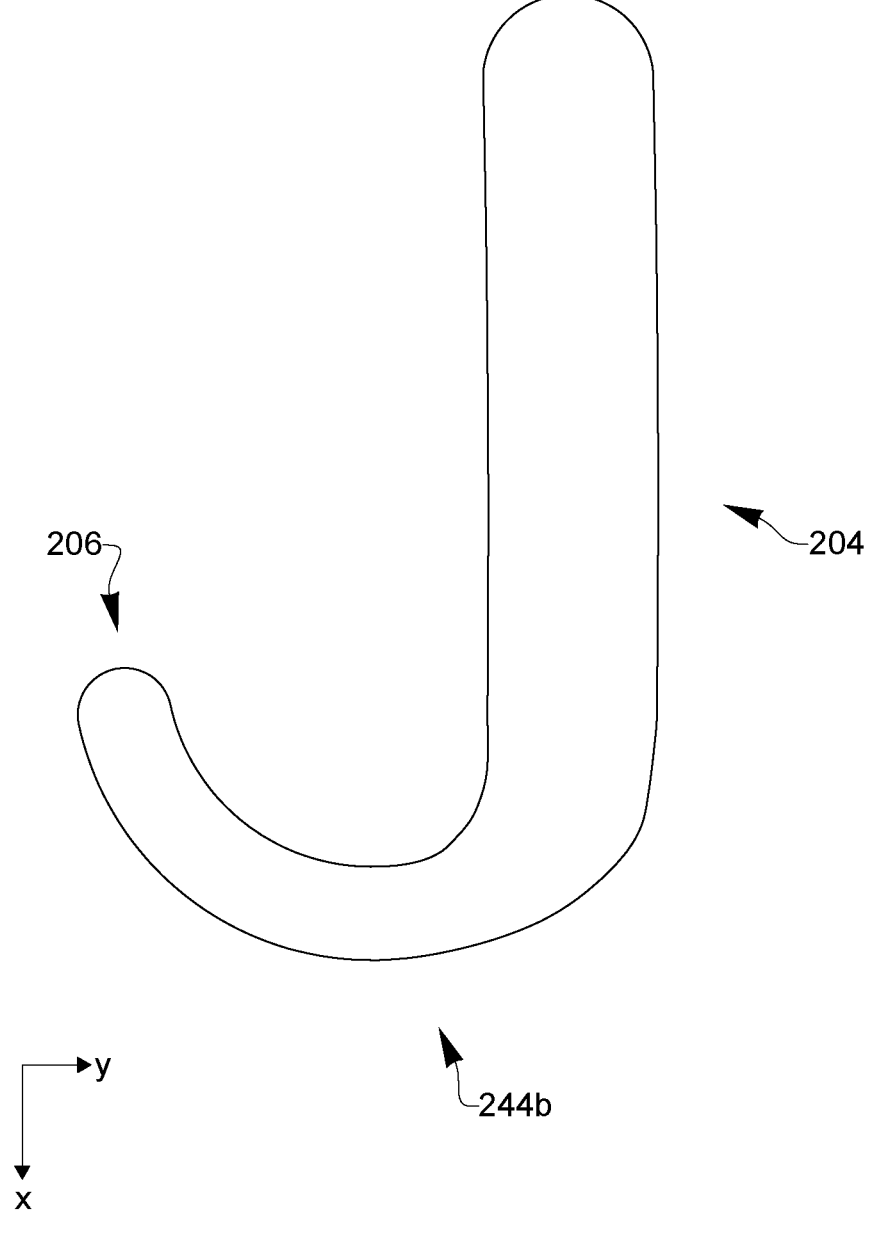
FIG. 10H is a bottom view of the embodiment of the dual panel assembly of FIG. 10A.
Figure 10I:
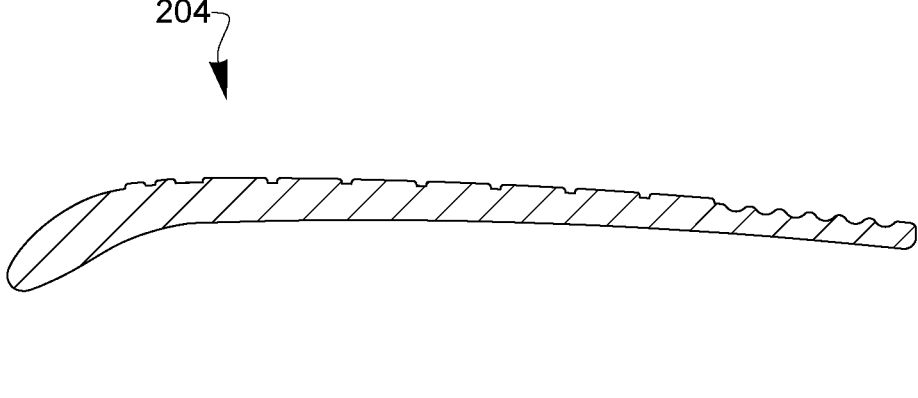
FIG. 10I is a cross-sectional view of the embodiment of the dual panel assembly taken along section line 10I-10I of FIG. 10F.
Figure 10J:
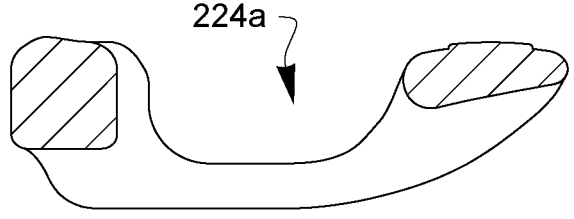
FIG. 10J is a cross-sectional view of the embodiment of the dual panel assembly taken along section line 10J-10J of FIG. 10G.
Figure 10J:
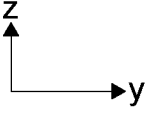
Figure 10K:
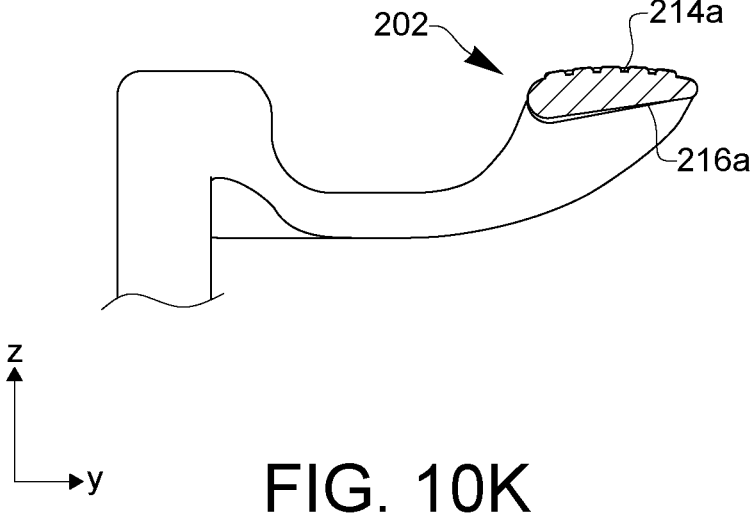
FIG. 10K is a cross-sectional view of the embodiment of the dual panel assembly taken along section line 10K-10K of FIG. 10E.
Figure 10L:
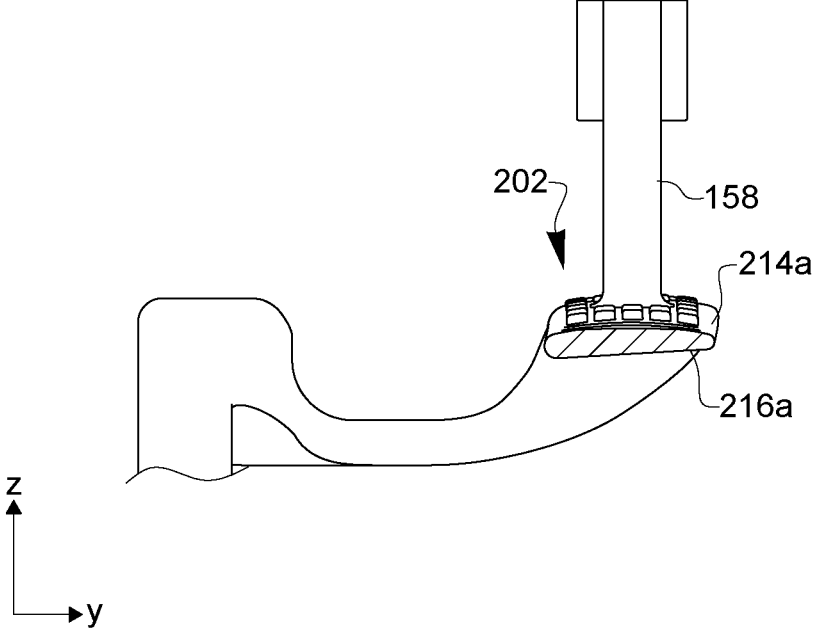
FIG. 10L is a cross-sectional view of the embodiment of the dual panel assembly taken along section line 10L-10L of FIG. 10E.

Referring to FIG. 10A, the dual panel assembly 200 may also include an upper yoke portion 224a that extends between the top panel 202 and a portion of the support column 206. As illustrated in FIG. 10C, the upper yoke portion 224a may extend from a first end 226a to a second end 228a. The first end 226a may be coupled to the proximal end 210a of the top panel 202, as illustrated in FIG. 10A, and the second end 228a may be coupled to a portion of the support column 206 at or adjacent to the top end 218 of the support column 206, as illustrated in FIG. 10B. As illustrated in FIG. 10G, the upper yoke portion 224a may extend from the first end 226a to the second end 228a along a first yoke axis 230a, which may be arcuate when viewed along the Z-axis of the reference coordinate system of FIG. 10A. With reference to FIG. 10C, the second end 228a of the upper yoke portion 224a includes an upper extension portion 232a that extends from a top end 233a to a bottom end 234a along an axis that is parallel to the column axis 222, and the top end 233a is at or adjacent to the top end 218 of the support column 206. A first support surface 236a is disposed at the top end 218 of the upper extension portion 232a, and the first support surface 236a may be aligned or substantially aligned (along a reference line parallel to the Y-axis of the plane of the reference coordinate system of FIG. 10A) with a portion of the upper surface 214a at or adjacent to the proximal end 210a of the top panel 202. The first support surface 236a may be planar or substantially planar, and may extend or generally extend normal to the column axis 222 and/or parallel to the X-Y plane of the reference coordinate system of FIG. 10A.

With reference to FIG. 10C, the first end 226a of the upper yoke portion 224a includes an upper post portion 238a that extends from a top end 239a to a bottom end 240a along an axis that is parallel to the column axis 222, and the top end 239a is coupled to a portion of the lower surface 216a of the top panel 202 at or adjacent to the proximal end 210a of the top panel 202. The bottom end 234a of the upper post portion 238a is aligned or substantially aligned (along a reference line parallel to the Y-axis of the plane of the reference coordinate system of FIG. 10A) with the bottom end 234a of the upper extension portion 232a.

The upper yoke portion 224a may also include a first strut member 242a that extends between the upper post portion 238a and the upper extension portion 232a, and the first strut member 242a may extend from a first end 244a to a second end 246a along the first yoke axis 230a. In particular, the first end 244a of the first strut member 242a may be coupled to a portion of the upper post portion 230a that is at or adjacent to the bottom end 240a of the upper post portion 230a. In addition, the second end 246a of the first strut member 242a may be coupled to a portion of the upper extension portion 232a that is at or adjacent to the bottom end 240a of upper extension portion 232a. When viewed along the X-axis of the reference coordinate system of FIG. 10A, the upper extension portion 232a, the upper post portion 238a, and the first strut member 242a cooperate to form a U-shape that defines a top recess 248a between the upper extension portion 232a and the upper post portion 238a and above the first strut member 242a, as illustrated in FIG. 10C. More specifically, the top recess 248a may be defined by an inner lateral surface 250a of the upper post portion 238a (which extends in a direction parallel to or substantially parallel to the Z-axis of the reference coordinate system of FIG. 10A), an opposing inner lateral surface 252a of the upper extension portion 232a (which extends in a direction parallel to or substantially parallel to the Z-axis of the reference coordinate system of FIG. 10A), and a top surface 254a of the first strut member 242a (which extends in a direction parallel to or substantially parallel to the Y-axis of the reference coordinate system of FIG. 10A).

Referring again to FIGS. 10A and 10B, the dual panel assembly 200 may also include the bottom panel 204, which may be identical to the top panel 202. That is, the bottom panel 204 may extend from a distal end 208b to a proximal end 210b along a longitudinal axis 212b that extends generally parallel to the X-axis of the reference coordinate system of FIG. 10A. The bottom panel 204 may be partially defined by an upper surface 214b that extends from the distal end 208b to the proximal end 210b of the bottom panel 204 along the longitudinal axis 212b. In some embodiments, the upper surface 214b may be planar and may extend along a plane parallel to the X-Y plane of the reference coordinate system of FIG. 10A. However, as illustrated in the left side view of FIG. 10E, the upper surface 214b, or a distal portion of the upper surface 214b, may have a cambered shape or the shape of an arc or segment of a circle when viewed along the Y-axis of the reference coordinate system of FIG. 10E (as illustrated in the cross-sectional view of FIG. 10I). The cambered shape or the shape of the arc or segment of the circle may be identical to that of the top panel 202. In some embodiments, a reference line 215b parallel to the X-axis of the reference coordinate system of FIG. 10A (that may also be parallel to the longitudinal axis 212a and/or the reference line 215a) may be tangent or approximately tangent to the upper surface 214b at or adjacent to the proximal end 208b. A plurality of textural features 156 may disposed over some or all of the upper surface 214b.

The bottom panel 204 may also be partially defined by a lower surface 216b that is opposite to the upper surface 214b, and the lower surface 216b may extend from the distal end 208b to the proximal end 210b of the bottom panel 204 along the longitudinal axis 212b. In embodiments in which the upper surface 214b may be planar, the lower surface 216b may also be planar and, for example, may extend along a plane parallel to the X-Y plane of the reference coordinate system of FIG. 10A. However, as illustrated in the left side view of FIG. 10E, the lower surface 216b may have the same or similar arc or cambered shape as the upper surface 214b such that the bottom panel 204 has a uniform or substantially uniform cross sectional shape (when viewed along the longitudinal axis 212a) from a point at or adjacent to the distal end 208b to a point at or adjacent to the proximal end 210b, which may be identical to the cross-sectional shape of the top panel 202 illustrated in FIGS. 10K and 10L. Also identical to the top panel 202, the lower surface 216b may be slightly angled such that in cross-section, when viewed along the parallel to the longitudinal axis 212b, the lower surface 216a is disposed at an acute angle to the Y-axis of the reference coordinate system of FIG. 10A.

Referring to FIG. 10A, the dual panel assembly 200 may also include a lower yoke portion 224b that extends between the bottom panel 204 and a portion of the support column 206. As illustrated in FIG. 10C, the lower yoke portion 224b may extend from a first end 226b to a second end 228b, and the lower yoke portion 224b may be identical or substantial identical to the upper yoke portion 224a. The first end 226b of the lower yoke portion 224b may be coupled to the proximal end 210b of the bottom panel 204, as illustrated in FIG. 10A, and the second end 228b may be coupled to a portion of the support column 206 at or adjacent to the bottom end 220 of the support column 206, as illustrated in FIG. 10B. As illustrated in FIG. 10G, the lower yoke portion 224b may extend from the first end 226b to the second end 228b along a second yoke axis 230b, which may be identical to, but offset from, the first yoke axis 230a of the upper yoke portion 224a. That is, the second yoke axis 230b may be arcuate when viewed along the Z-axis of the reference coordinate system of FIG. 10A. With reference to FIG. 10C, the second end 228b of the second yoke axis 230b includes a lower extension portion 232b that extends from a top end 233b to a bottom end 234b along an axis that is parallel to the column axis 222, and the bottom end 233a extends up to or beyond the bottom end 220 of the support column 206. A second support surface 236b is disposed at the top end 233b of the lower extension portion 232a, and the second support surface 236b may be aligned or substantially aligned (along a reference line parallel to the Y-axis of the plane of the reference coordinate system of FIG. 10A) with a portion of the upper surface 214b of the bottom panel 204 at or adjacent to the proximal end 210b of the bottom panel 204. The second support surface 236b may be planar or substantially planar, and may extend or generally extend normal to the column axis 222 and/or parallel to the X-Y plane of the reference coordinate system of FIG. 10A.

With reference to FIG. 10C, the first end 226b of the lower yoke portion 224b includes a lower post portion 238b that extends from a top end 239b to a bottom end 240b along an axis that is parallel to the column axis 222, and the top end 239b is coupled to a portion of the lower surface 216b of the bottom panel 204 at or adjacent to the proximal end 210b of the bottom panel 204. The bottom end 234b of the lower post portion 238b is aligned or substantially aligned (along a reference line parallel to the Y-axis of the plane of the reference coordinate system of FIG. 10A) with the bottom end 234b of the lower extension portion 232b.

The lower yoke portion 224b may also include a second strut member 242b that extends between the lower post portion 238b and the lower extension portion 232b, and the second strut member 242b may extend from a first end 244b to a second end 246b along the second yoke axis 230b. In particular, the first end 244b of the second strut member 242b may be coupled to a portion of the lower post portion 230b that is at or adjacent to the bottom end 240b of the lower post portion 230b. In addition, the second end 246b of the second strut member 242b may be coupled to a portion of the lower extension portion 232b that is at or adjacent to the bottom end 240b of lower extension portion 232b. When viewed along the X-axis of the reference coordinate system of FIG. 10A, the lower extension portion 232b, the lower post portion 238b, and the second strut member 242b cooperate to form a U-shape that defines a bottom recess 248b between the lower extension portion 232b and the lower post portion 238b and above the second strut member 242b, as illustrated in FIG. 10C. More specifically, the bottom recess 248b may be defined by an inner lateral surface 250b of the lower post portion 238b (which extends in a direction parallel to or substantially parallel to the Z-axis of the reference coordinate system of FIG. 10A), an opposing inner lateral surface 252b of the lower extension portion 232b (which extends in a direction parallel to or substantially parallel to the Z-axis of the reference coordinate system of FIG. 10A), and a top surface 254b of the second strut member 242b (which extends in a direction parallel to or substantially parallel to the Y-axis of the reference coordinate system of FIG. 10A).

Figure 7A:
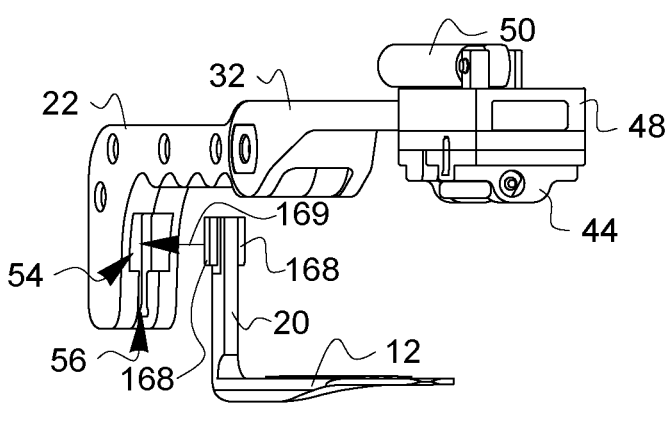
FIGS. 7A-7C are a series of perspective views illustrating operational steps showing the loading of the left sternal ascender of FIG. 5 into the sternal ascender apparatus of FIG. 1.
Figure 7B:
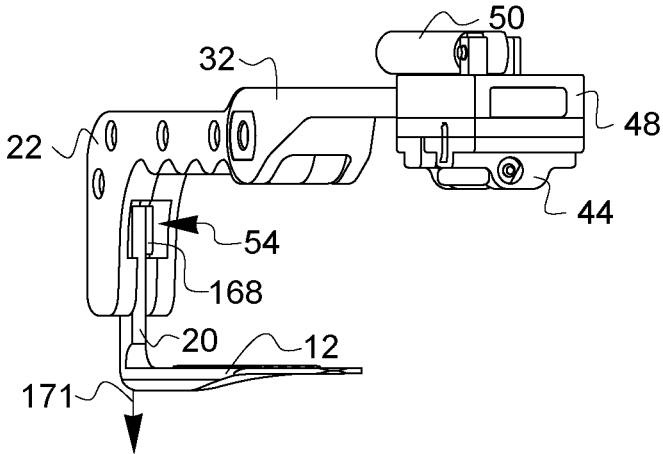
Figure 7C:
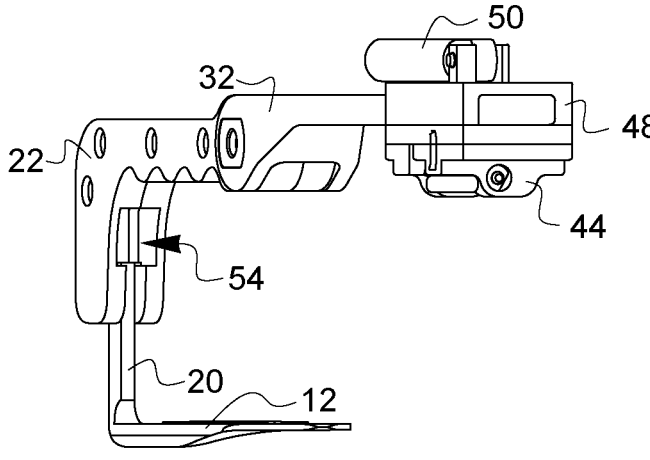

FIGS. 7A-7C are a series of perspective views illustrating operational steps showing the loading of the left sternal ascender of FIG. 5 into the sternal ascender apparatus of FIG. 1. The appropriate sternal ascender, left or right, is selected depending on the area of interest for a minimally invasive surgical procedure requiring the sternum of a patient to be lifted upward. FIG. 7A shows the right sternal ascender 12 aligned with and in proximity to the t-slot 54 of the indicator handle 22 of the sternal elevator apparatus 10 with the orientation features 168 on the post 20 of the right sternal ascender 12 moved towards direction 169 and fully inserted into the slot 54 of the indicator handle 22. Once inserted, as shown in FIG. 7B, the right sternal ascender 12 is pulled downward in direction 171 towards the seat 56 in the slot 54 of the indicator handle 22 to lock the right sternal ascender 12 into place. FIG. 7C shows the fully inserted and locked right sternal ascender 12 in the indicator handle 22.

Figure 8:
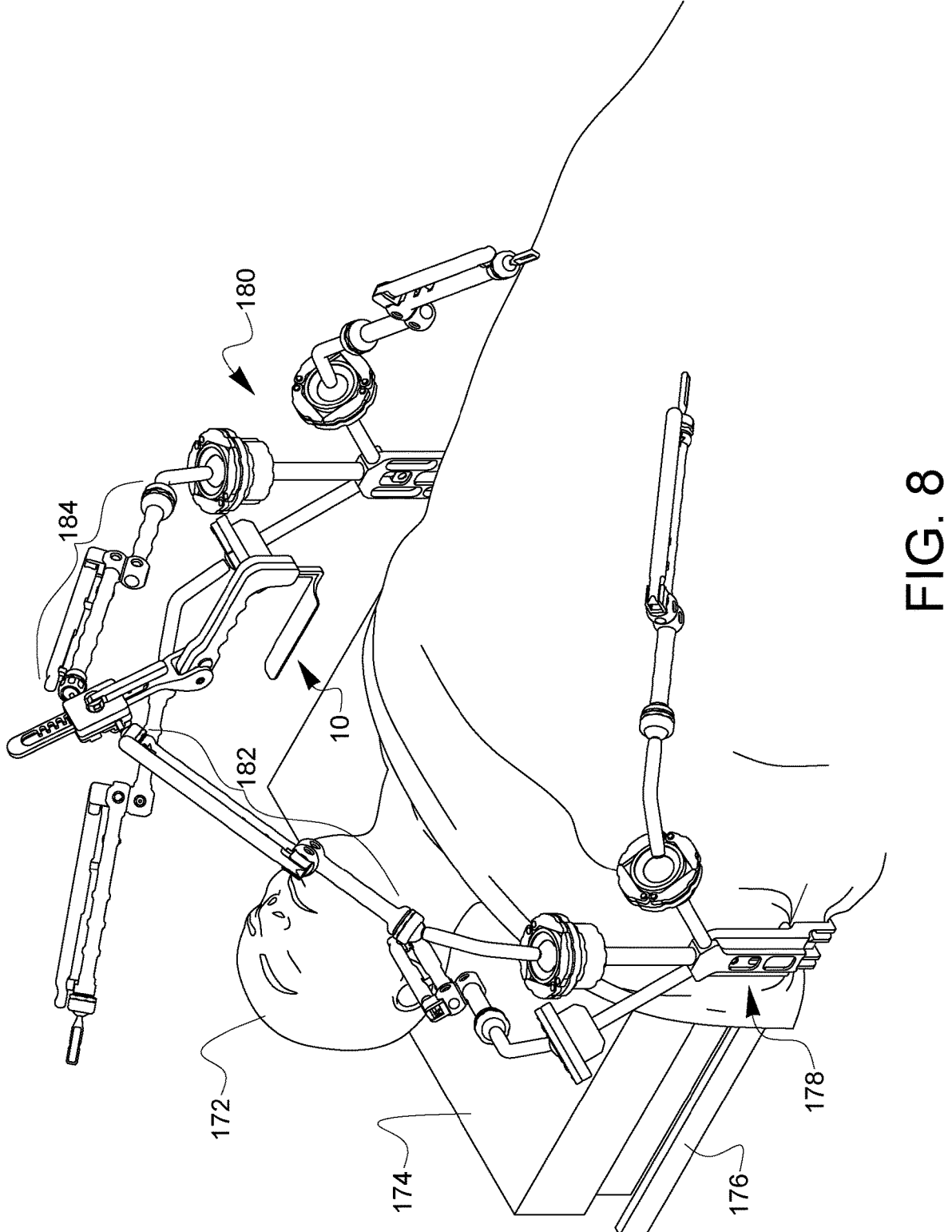
FIG. 8 is a perspective view of a surgical setting including the use of the sternal ascender apparatus of FIG. 1.

FIG. 8 is a perspective view of a surgical setting including the use of the sternal ascender apparatus of FIG. 1. In the illustrated surgical setting, an operating table 174 having a rail 176 and a patient 172 on the table 174 prepared for a surgical procedure are shown. Positioned on the rail 176 is a first surgical equipment holder apparatus 178 having a first central surgical equipment holder 182 attached to the first surgical equipment holder apparatus 178. The first surgical equipment holder apparatus 178 is attached to the sternal ascender apparatus 10 at the first adapter channel 46. On an opposite side of the table, a second surgical equipment holder apparatus 180 is attached to an opposite rail, which is not visible here. The second surgical equipment holder apparatus 180 has a second central surgical equipment holder 184 attached thereto and is also attached to the corresponding second adapter channel on the sternal ascender apparatus 10 on its opposite side, not visible here. Each of the first central surgical equipment holder 182 and the second central surgical equipment holder 184 can be utilized to position and hold one or more pieces of surgical equipment or tools such as the sternal ascender apparatus 10 or alternatively scope holders, cannulas, or other surgical implements during a minimally invasive or other surgical procedure. In this configuration, the first central surgical equipment holder 182 and the second central surgical equipment holder 184 are shown bridging over the patient 172 in order to firmly position the sternal ascender apparatus 10 in an initial centralized location relative to the patient 172 on the table 174.

The dual panel assembly 200 may be used in any suitable procedure that involves lifting a portion of the sternum of a patient. For example, the dual panel assembly 200 may be used in a left thoracotomy for MIDCAB (Minimally Invasive Direct-View Coronary Artery Bypass) vessel harvest. The bottom panel 204 may be insertable in a small incision, such as an incision in the 4th or 5th intercostal space on the left chest. With the bottom panel 204 so inserted, the upper surface 214b of the bottom panel 204 may be positioned on an interior-facing portion of the patient's sternum. In addition, the second support surface 236b of the lower extension portion 232b of the lower yoke portion 224b may engage a portion of a rib adjacent to the 4th or 5th intercostal space (e.g., if the 4th interspace was selected for the incision, the second support surface 236b would interface with the 5th rib posteriorly) to provide additional stability to the dual panel assembly 200. The dual panel assembly 200, which is coupled to the sternal ascender apparatus 10 by the mounting post 20, 158 as described, may be used to elevate the sternum of the patient to allow for easier access when harvesting vessels, and the "support bridge" established by the second support surface 236b contacting the rib and the upper surface 214b of the bottom panel 204 contacting the sternum distributes the force during retraction. Further, the bottom recess 248b defined in the lower yoke portion 224b may allow the surgeon to insert instruments through the incision and then through the bottom recess 248b to access the left internal thoracic artery (LITA). The bottom recess 248b also protects the LITA during retracting.

In addition, with the bottom panel 204 and the lower yoke portion 224b inserted as described, the top panel 202 (and upper yoke portion 224a) remains outside of and elevated from the patient's incision and is therefore fully visible by the surgeon. Because the top panel 202 (and upper yoke portion 224a) are identical to the bottom panel 204 (and the lower yoke portion 224b). the top panel 202 acts as a "replicator panel" and allows the surgeon to visualize the exact positioning and orientation of the bottom panel 204 that is inside the patient, which improves the surgeon's ability to properly position the bottom panel 204 and the lower yoke portion 224b.

Figure 9A:
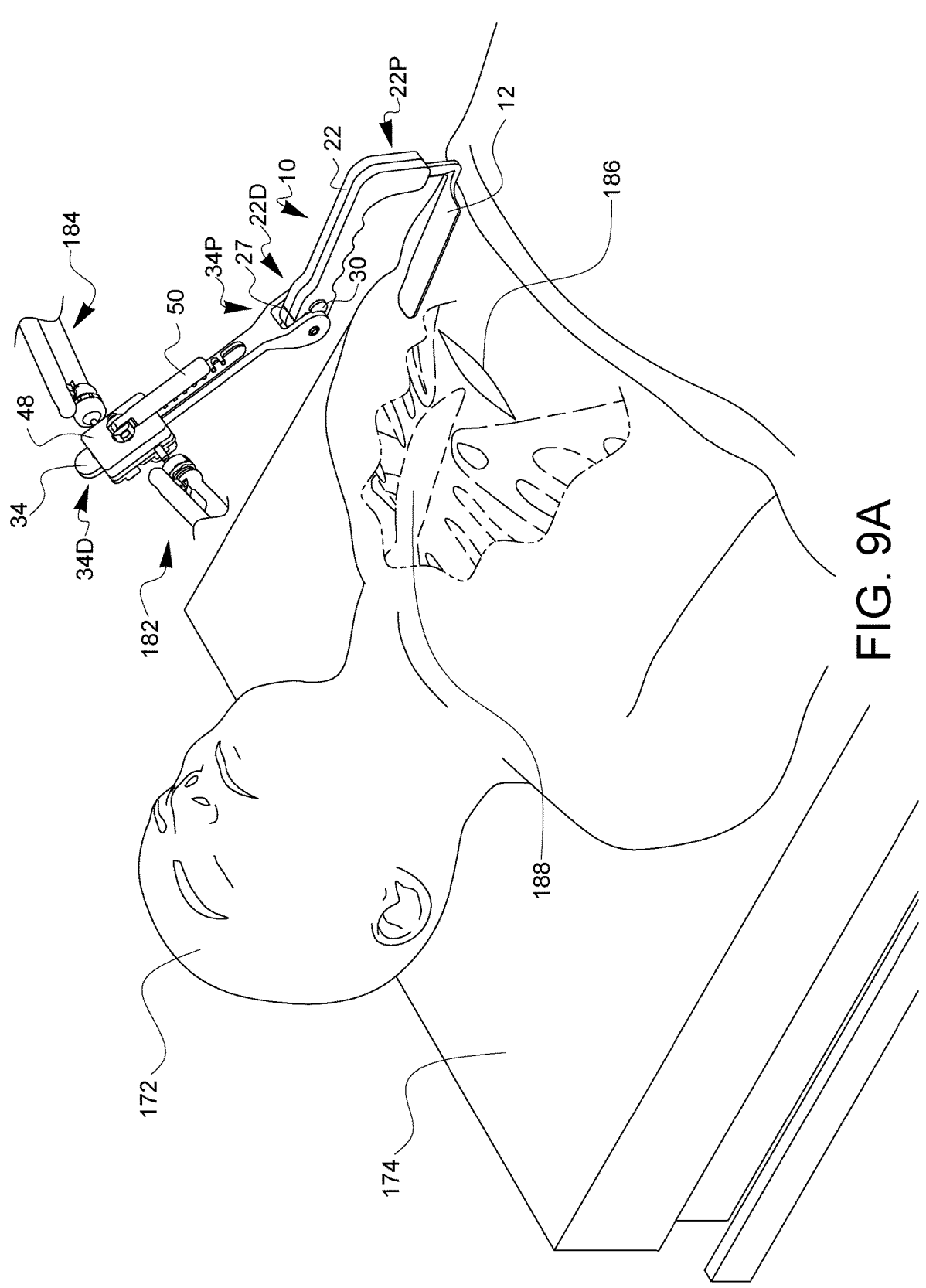
FIGS. 9A-9D are a series of perspective views illustrating operational steps of the use of the sternal ascender apparatus in a surgical context.
Figure 9B:
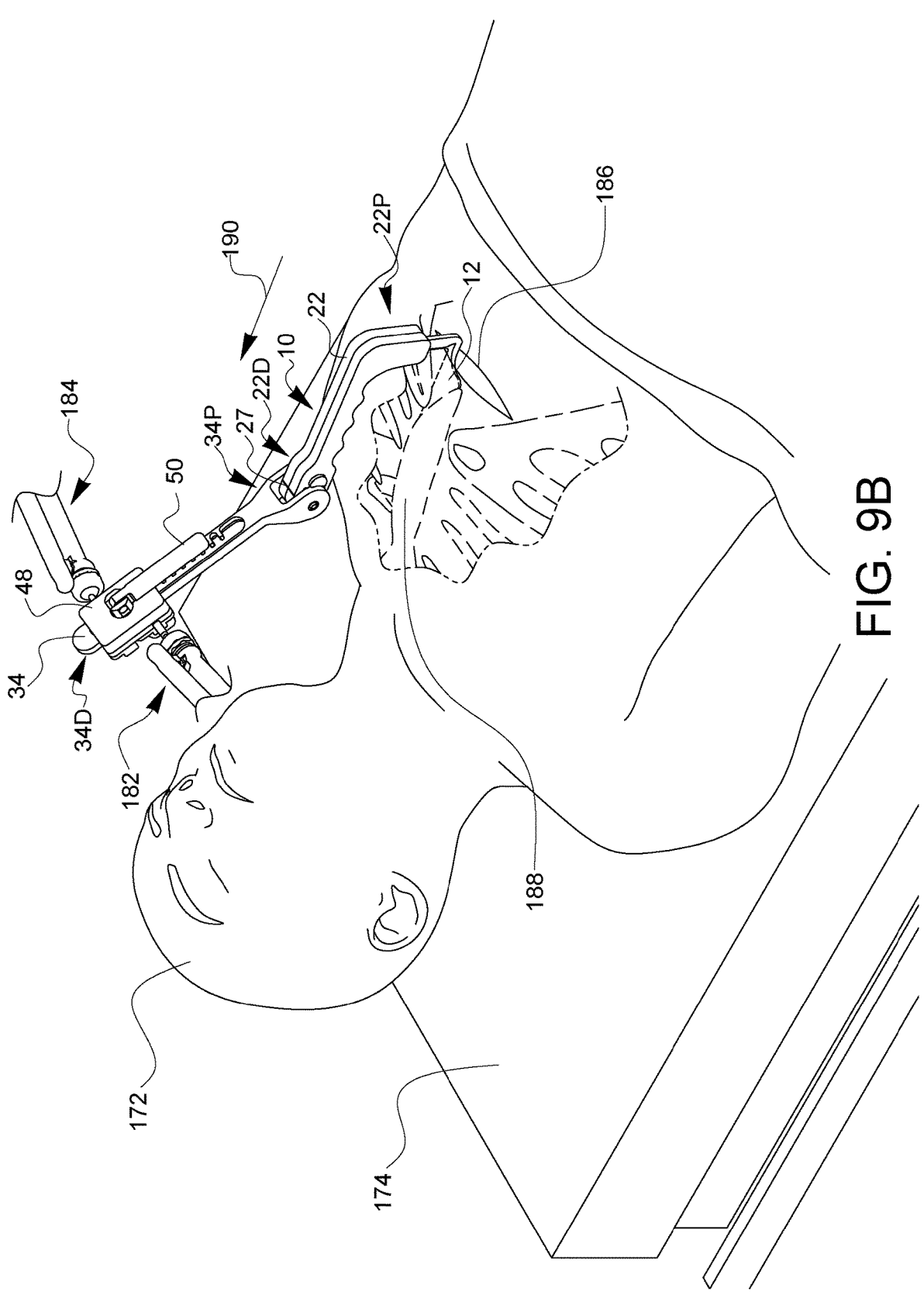
Figure 9C:
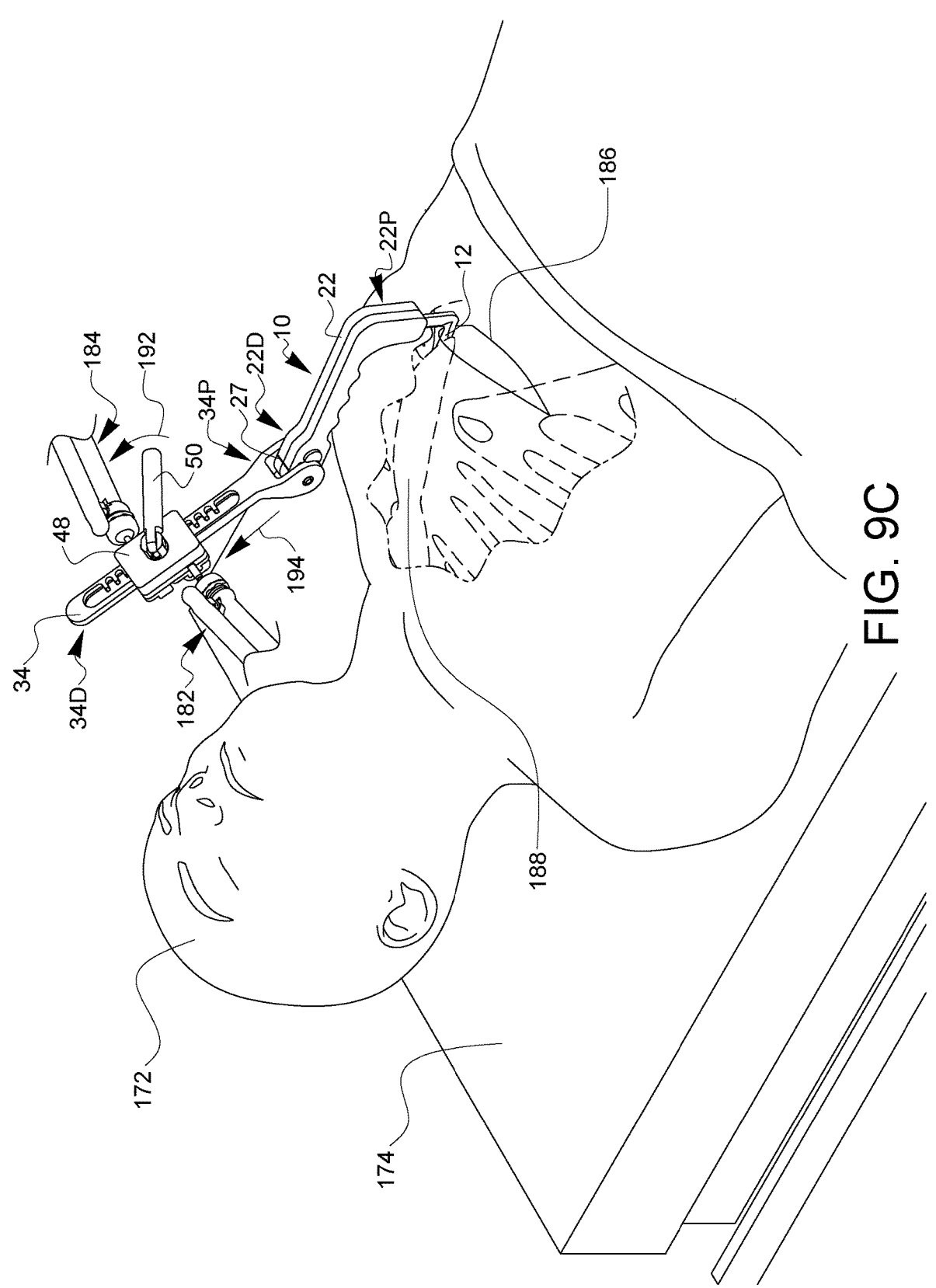
Figure 9D:
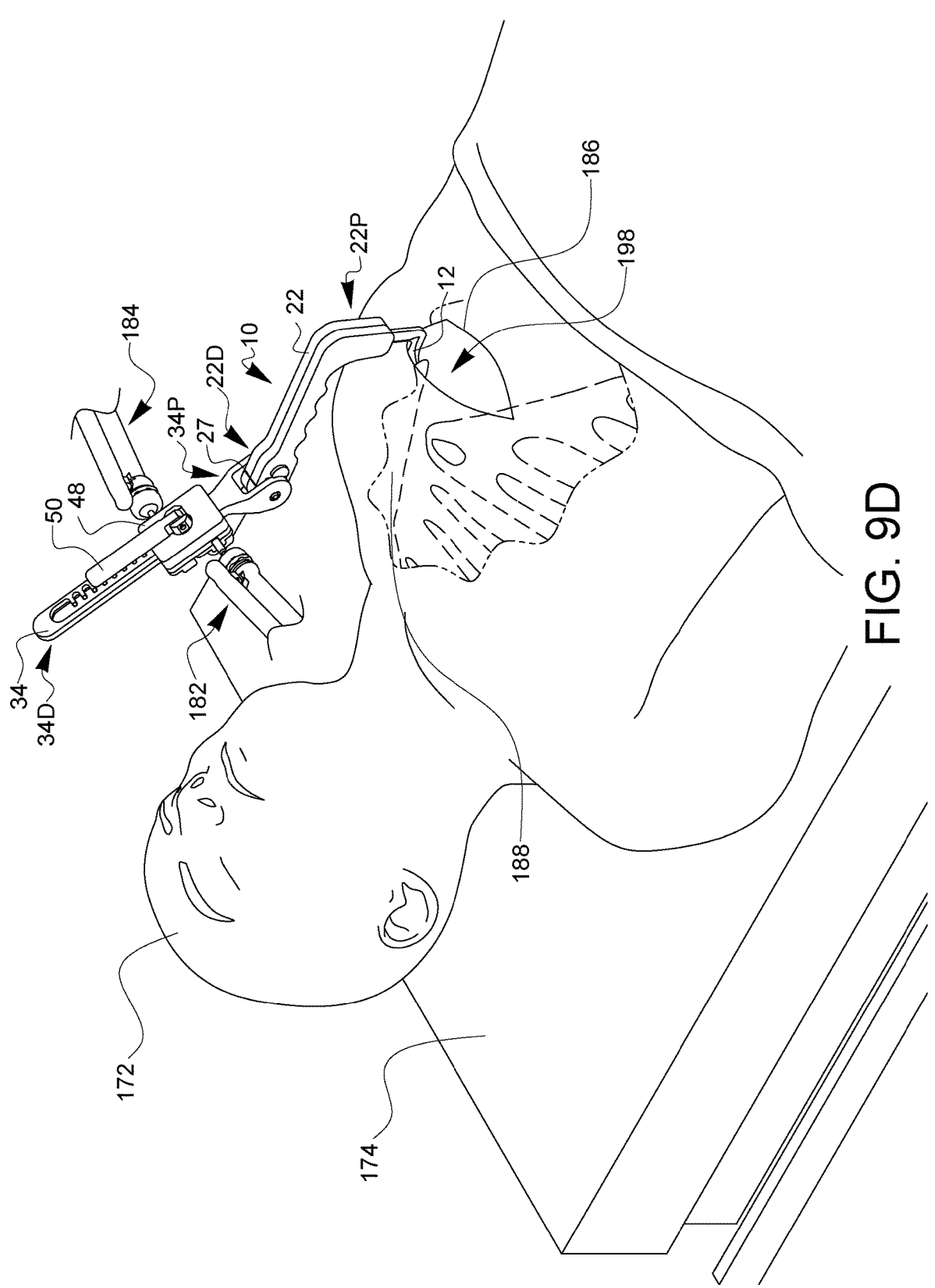

FIGS. 9A-9D are a series of perspective views illustrating operational steps of the use of the sternal ascender apparatus in a surgical context. In FIGS. 9A-9D, portions of the patient 172 are shown in cross-section and portions of various instrumentation are removed from view for the purposes of clarity. The patient 172 is shown prepped for a surgical procedure, having an incision 186 made at just below the xiphoid process at the sternal notch, near the sternum 188. The sternal elevator apparatus 10 is secured onto the first central surgical equipment holder 182 and the second central surgical equipment holder 184, which are firmly mounted onto the operating table 174. The upper rack housing 48, or the arch keystone is at the top of the toothed linear rack and thus enables subsequent movement of the rack 34 upward. The angle of the indicator handle 22 and therefore the sternal ascender 12 has been adjusted by pressing the pivot button or pressable switch 30 on the indicator handle 22, allowing movement of the indicator handle 22 relative to the linear actuator gear 34. As shown in FIG. 9B, the distal end 12D of the sternal ascender 12 is inserted in direction 190 into the incision 186 until the sternal ascender 12 is in a desired location along the sternum 188. The sternal ascender 12 is aligned with the anatomy of the sternum 188 by using the depth indicator 27 to gauge the location of the tip of the panel of the sternal ascender 12 within the chest. At this point, the first central surgical equipment holder 182 and the second central surgical equipment holder 184 are locked and secured into place after proper adjustment. FIG. 9C illustrates the swivel bar 50 being unlocked and moved counterclockwise 192 to raise the sternal ascender 12 and indicator handle 22 in direction 194, which applies retraction to the sternum 188 and creates the subxiphoid space 198 for access. A final state of this described procedure is illustrated in FIG. 9D, at which time the swivel bar 50 can be moved to a full up or down position to lock the gear housing 48 in place to prevent any further movement of the sternal ascender 12.

FIGS. 11A to 11H are various views of a further embodiment of a sternal assembly, i.e., a panel member 300, that is configured to be coupled to the sternal ascender apparatus 10. The panel member 300 may include a panel portion 302 and a support portion 304. The panel portion 302 may extend from a distal end 306 to a proximal end 308 along a longitudinal axis 310 that extends generally parallel to the X-axis of the reference coordinate system of FIG. 11G. As illustrated in the top view of FIG. 11E, the panel portion 302 may be partially defined by a first lateral edge 312 and an opposing second lateral edge 314, and the first lateral edge 312 4 may generally extend from the proximal end 308 to the distal end 306 of the panel portion 302 along the X-axis of the reference coordinate system of FIG. 11G. The second lateral edge 314 may generally extend from a proximal end 315 offset from the proximal end 308 of the panel portion 302 to the distal end 306 of the panel portion 302 parallel to or substantially parallel to the X-axis of the reference coordinate system of FIG. 11G.

The panel portion 302 may also be partially defined by a distal edge 316 disposed at the distal end 306 of the panel portion 302 that extends parallel or substantially parallel to the Y-axis of the reference coordinate system of FIG. 11G. In particular, the distal edge 316 may extend from a distal end of the first lateral edge 312 to a distal end of the second lateral edge 314. The distal edge 316 may have any suitable shape, such as a generally arcuate shape or the shape of an arc or segment of a circle (when viewed along an axis parallel to the Z-axis of the reference coordinate system of FIG. 11G.

Figure 11A:
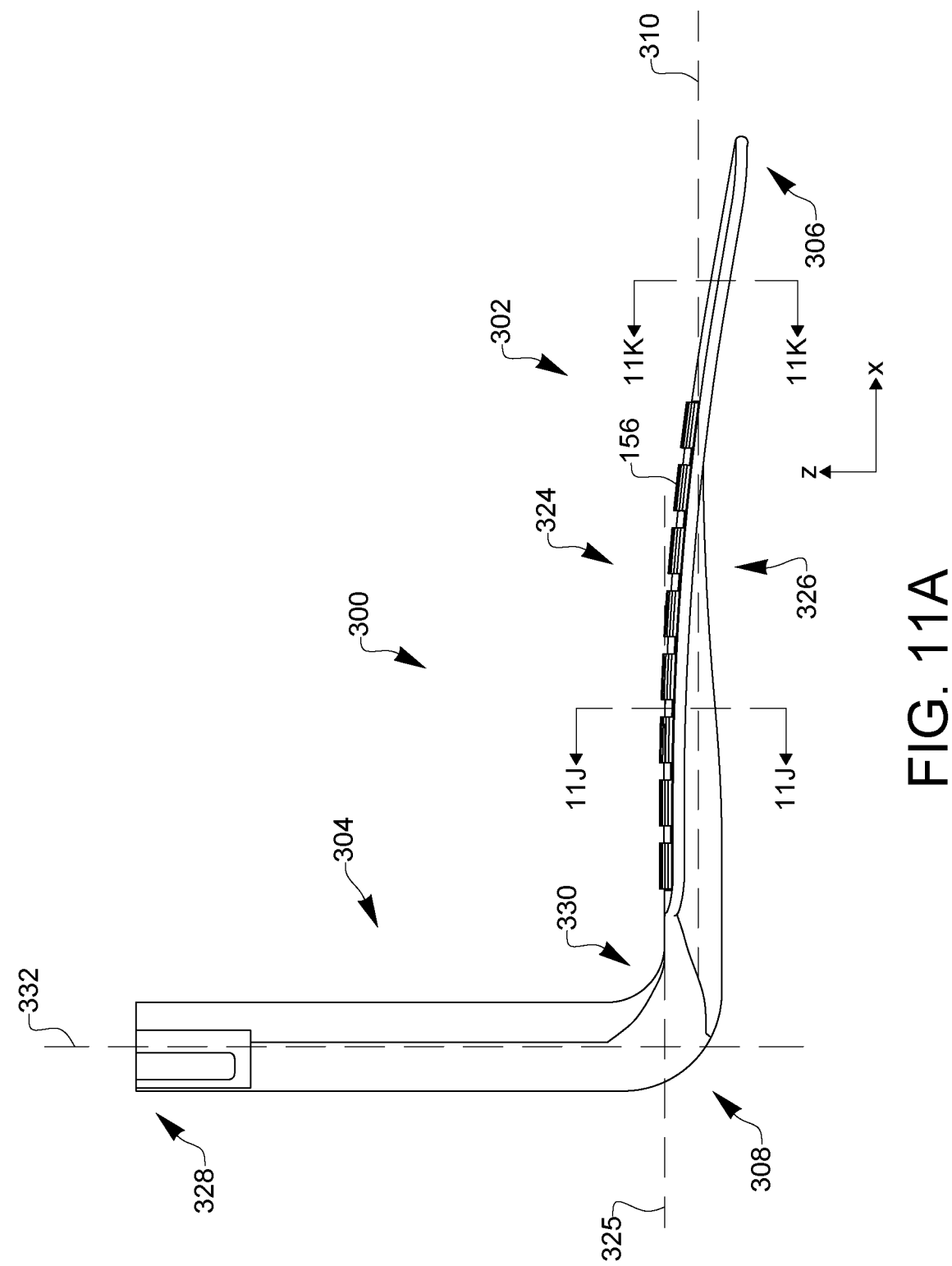
FIG. 11A is a first side view of a further embodiment of a panel member that is configured to be coupled to the sternal ascender apparatus.
Figure 11B:
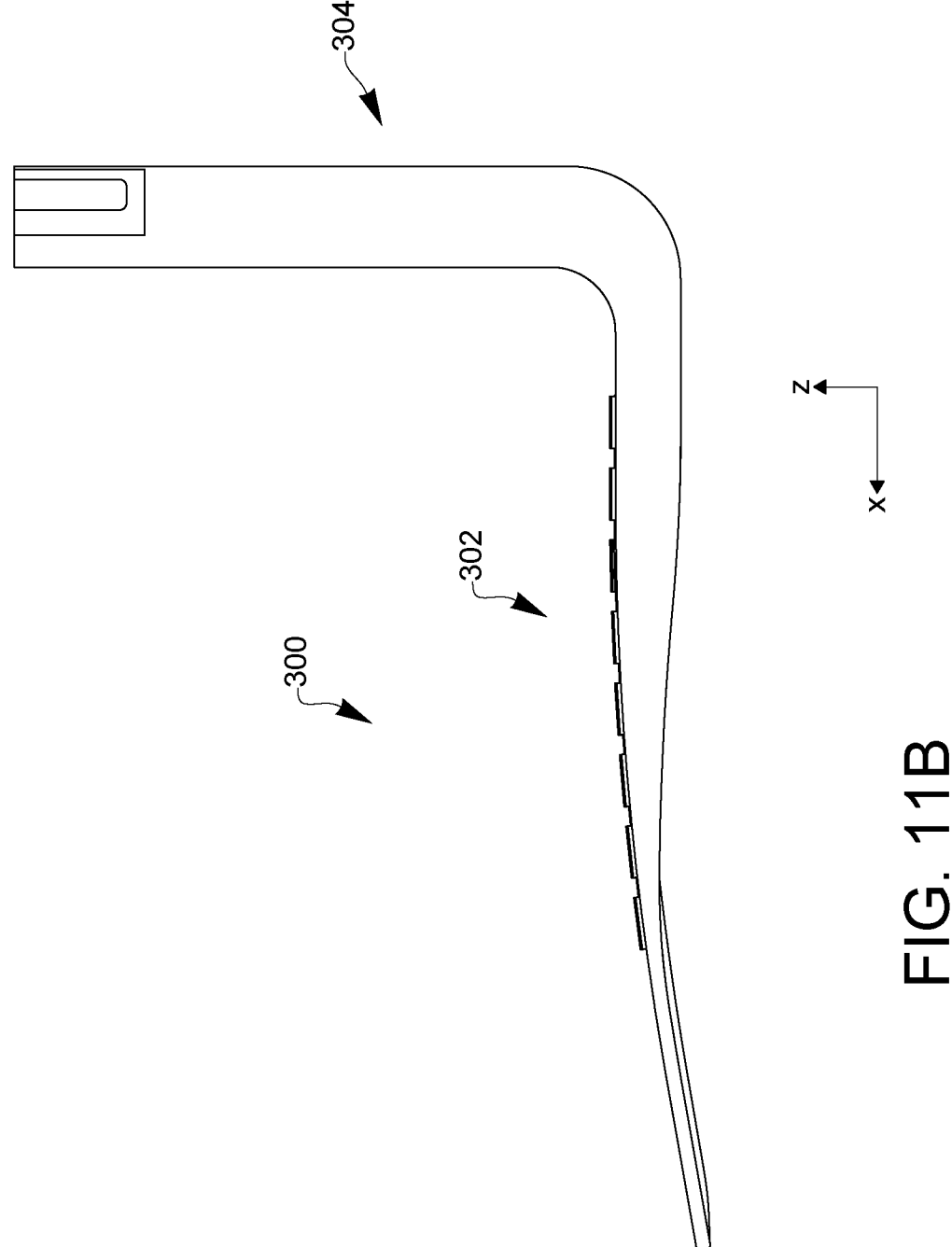
FIG. 11B is a second side view of the embodiment of the panel member of FIG. 11A.
Figure 11D:
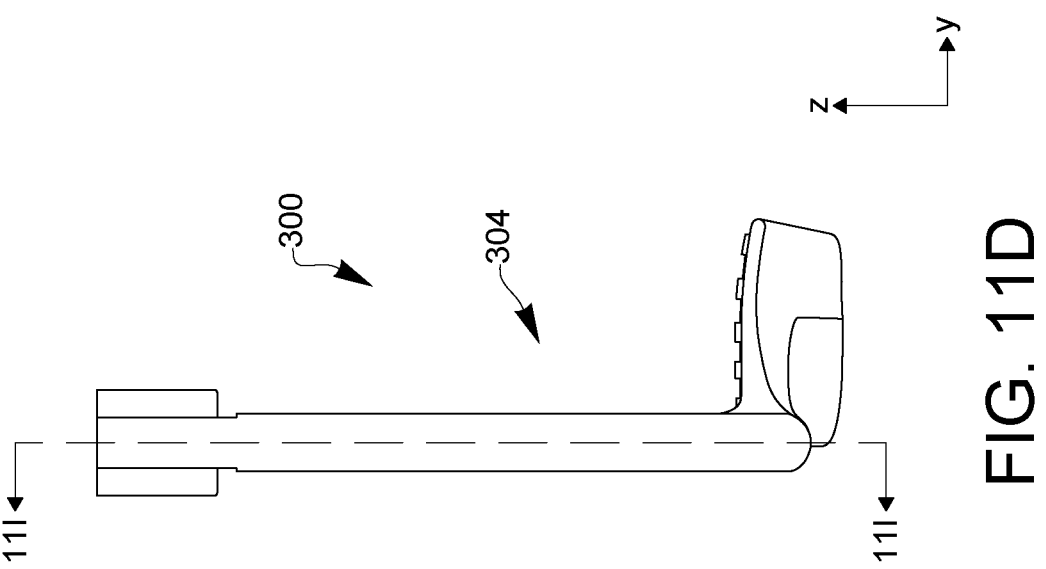
FIG. 11D is a rear view of the embodiment of the panel member of FIG. 11A.
Figure 11C:
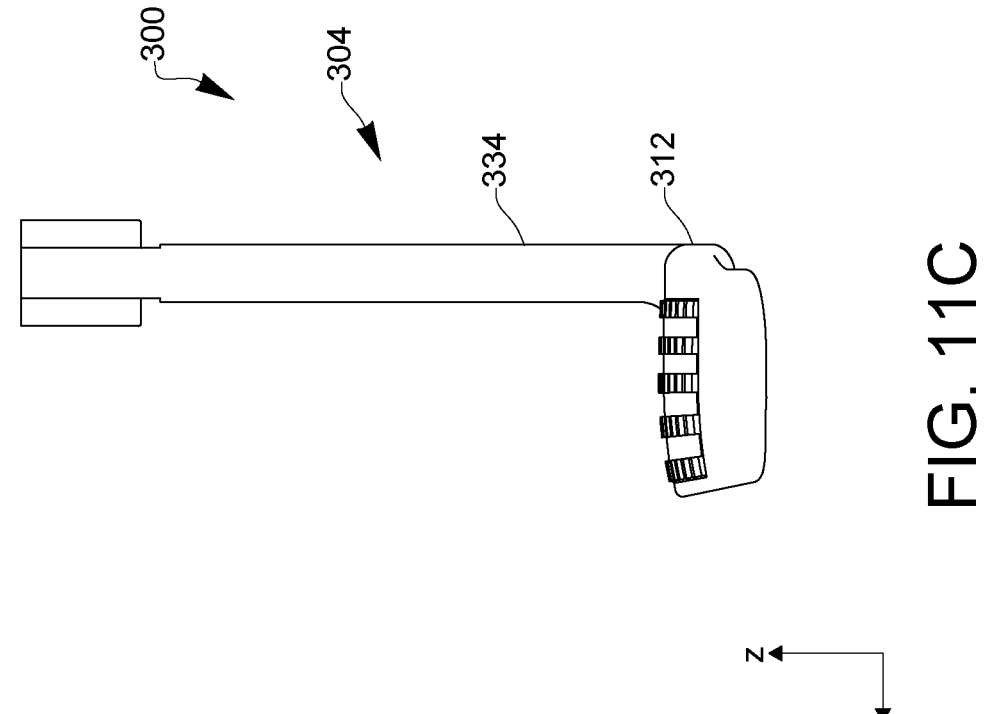
FIG. 11C is a front view of the embodiment of the panel member of FIG. 11A.
Figures 11E, 11F:
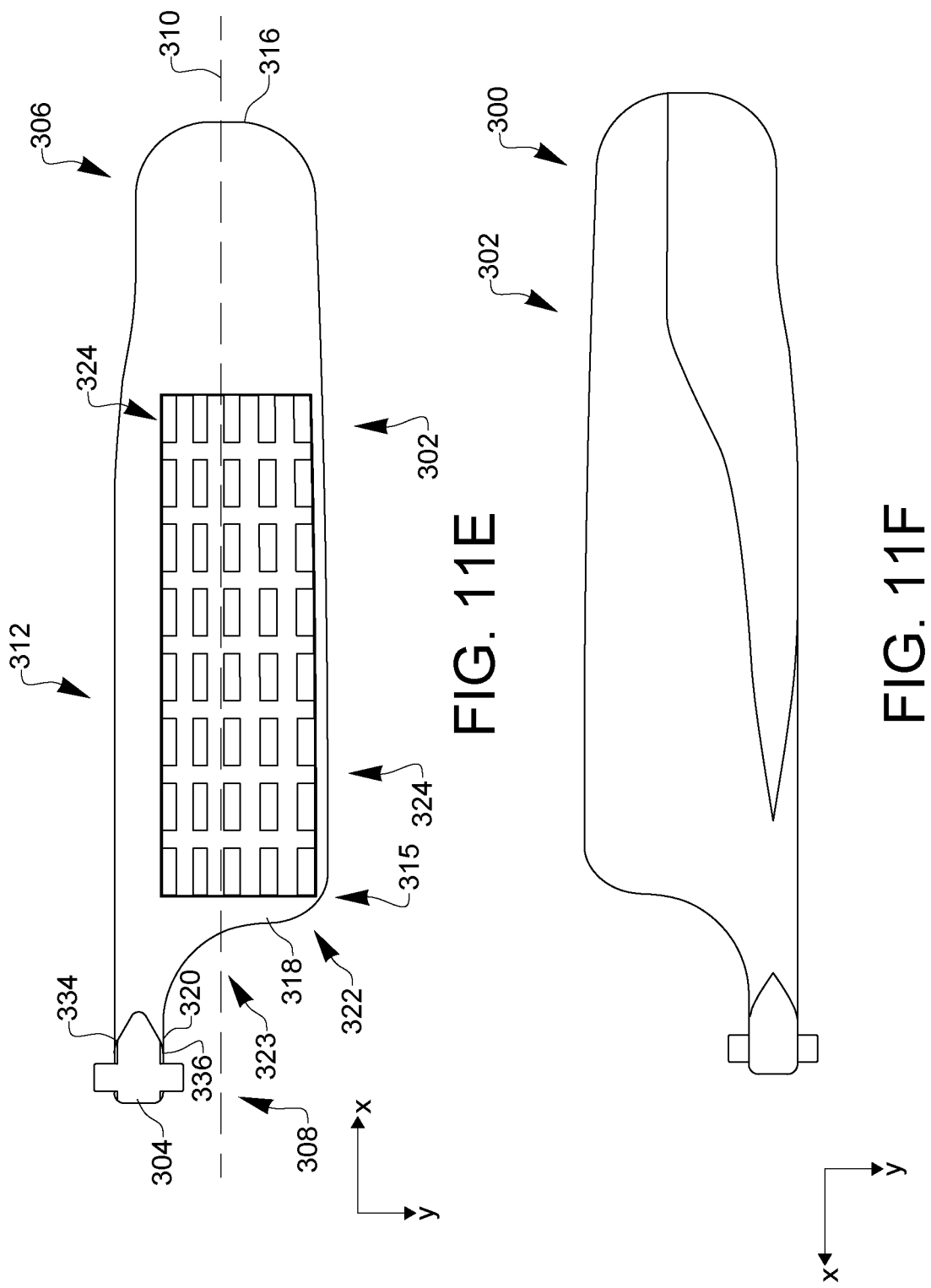
FIG. 11E is a top view of the embodiment of the panel member of FIG. 11A.
FIG. 11F is a bottom view of the embodiment of the panel member of FIG. 11A.
Figure 11H:
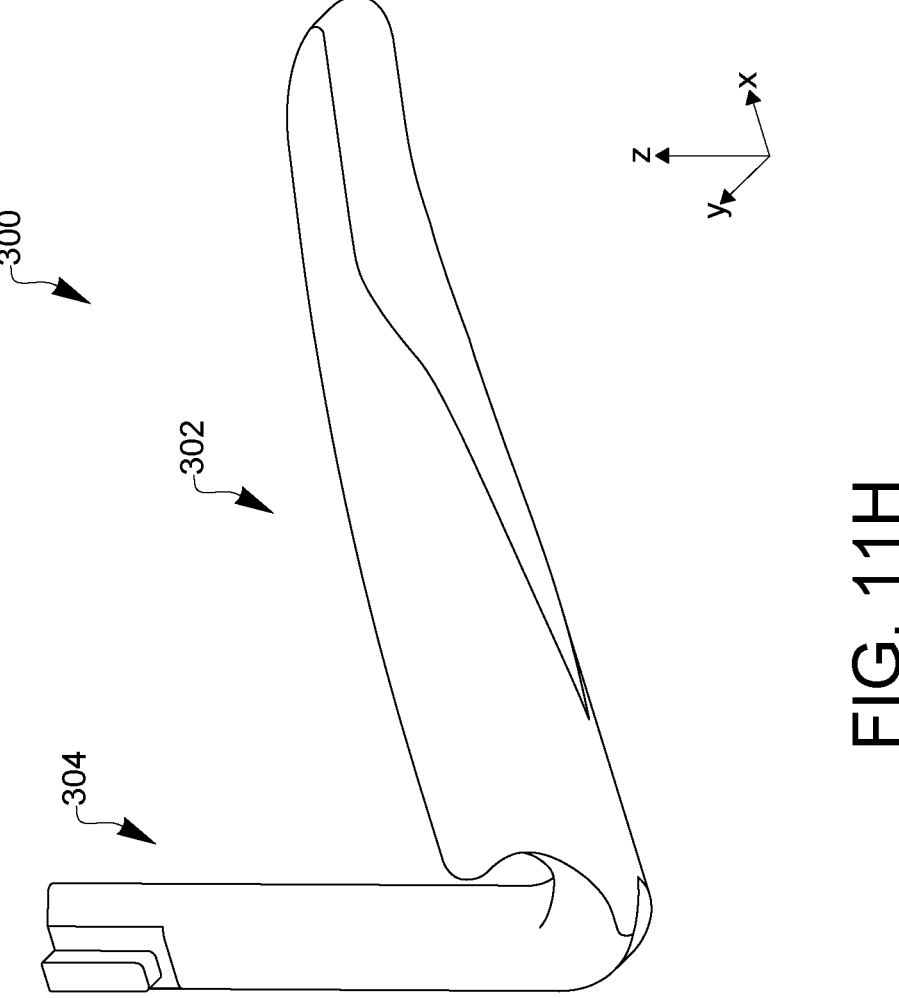
FIG. 11H is a second perspective view of the embodiment of the panel member of FIG. 11A.

The panel portion 302 may further be partially defined by a proximal edge 318 disposed offset from the proximal end 308 of the panel portion 302 that extends from a first point 322 at or adjacent to the proximal end 315 of the second lateral edge 314 to a second point 323, and the proximal edge 318 extends towards the first lateral edge 312 parallel to or substantially parallel to the Y-axis of the reference coordinate system of FIG. 11E. An inner lateral edge 320 extends from the second point 323 of the proximal edge 318 to an end point at or adjacent to the proximal end 308 of the panel portion 302, and the inner lateral edge 320 may extend parallel to or substantially parallel to the X-axis of the reference coordinate system of FIG. 11G.

Figure 11I:
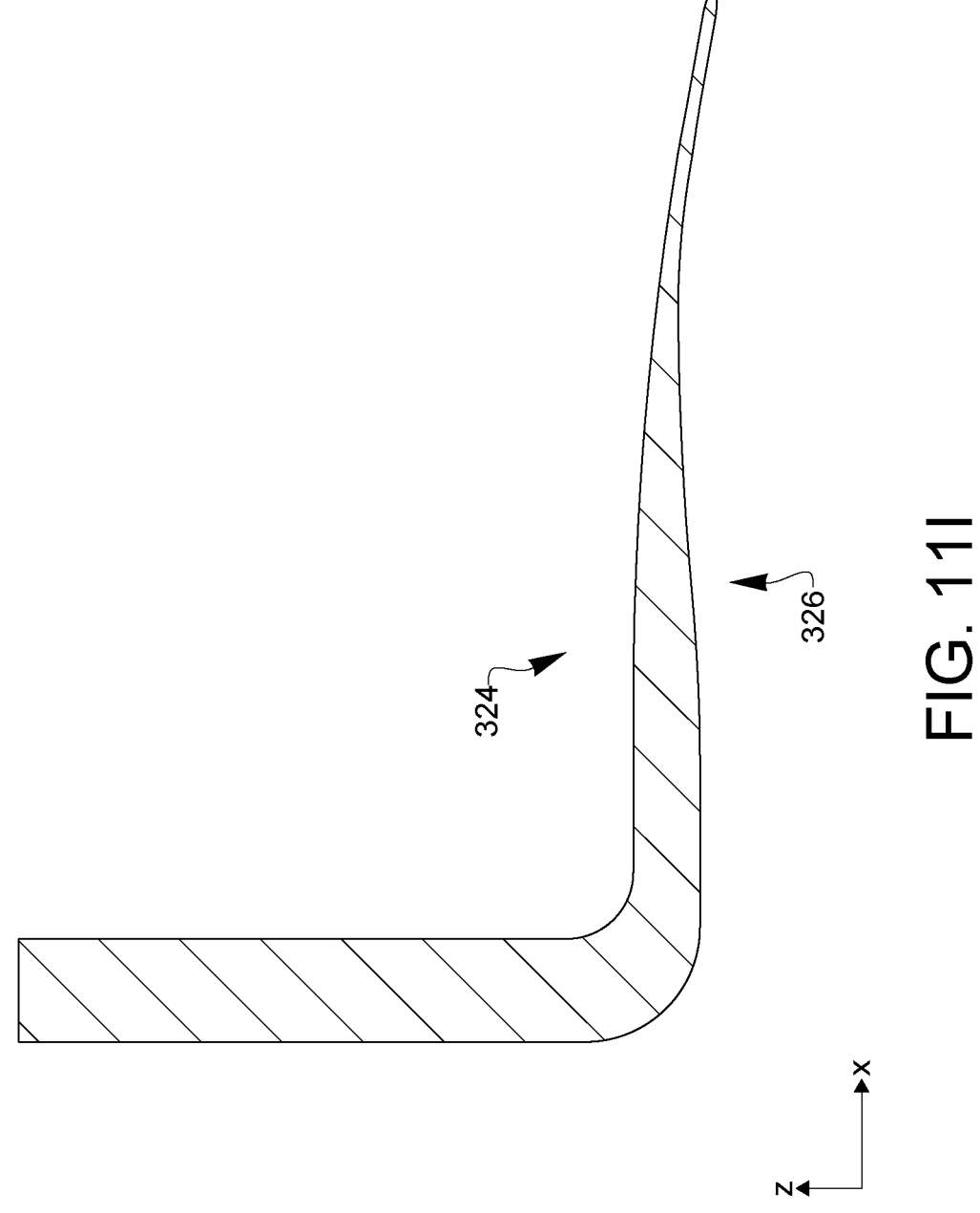
FIG. 11I is a cross-sectional view of the embodiment of the panel member taken along section line 11I-11I of FIG. 11D.
Figure 11K:
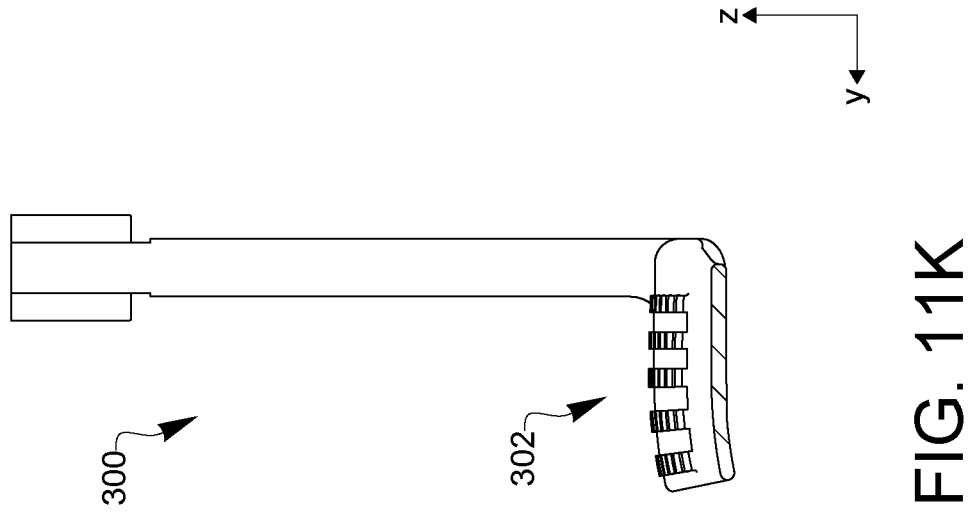
FIG. 11K is a cross-sectional view of the embodiment of the panel member taken along section line 11K-11K of FIG. 11A.

The first lateral edge 312, the second lateral edge 314, the distal edge 316, the proximal edge 318, and the inner lateral edge 320 may define an upper surface 324 that extends from the distal end 306 to the proximal end 308 of the panel portion 302 along the longitudinal axis 310. In some embodiments, the upper surface 324 may be planar and may extend along a plane parallel to the X-Y plane of the reference coordinate system of FIG. 11G. However, as illustrated in the side view of FIG. 11A, the upper surface 324 of the panel portion 302, or a distal portion of the upper surface 324, may have a cambered shape or the shape of an arc or segment of a circle when viewed along the Y-axis of the reference coordinate system of FIG. 11G (also, illustrated in the cross-section of the panel portion 302 in FIG. 11I). In some embodiments, a reference line 325 parallel to the X-axis of the reference coordinate system of FIG. 11G (that may also be parallel to the longitudinal axis 310) may be tangent or approximately tangent to the upper surface 324 at or adjacent to the proximal end 308. A plurality of textural features 156 may disposed over some or all of the upper surface 324. The proximal edge 318 and the inner lateral edge 320 may cooperate to define a notch 336 in the proximal end 308 of the panel portion 302, and the notch 336 is similar or identical to the notch 16 previously described.

Figure 11J:
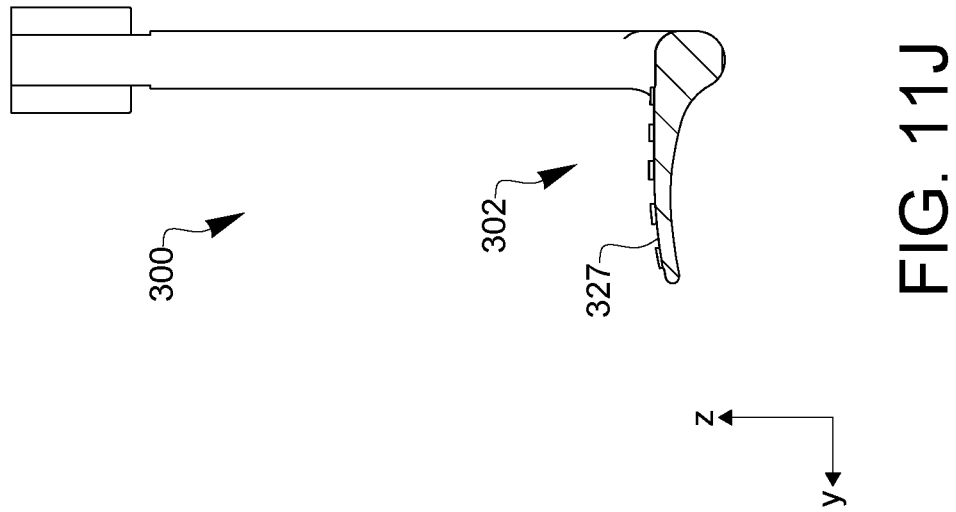
FIG. 11J is a cross-sectional view of the embodiment of the panel member taken along section line 11J-11J of FIG. 11A.

As illustrated in the cross-sectional view of FIG. 11J, the upper surface 324 of the panel portion 302, or a distal portion of the upper surface 324, may extend along a cross-reference line 327 that may have a cambered shape or the shape of an arc or segment of a circle when viewed along the X-axis of the reference coordinate system of FIG. 11G. Accordingly, the upper surface 324 of the panel portion 302 may include a compound curve that bends along two axes or two planes. Such complex curvature allows the upper surface 324 of the panel portion 302 to conform to the shape of the internal surface of a patient's sternum to distribute pressure when the panel member 300 is used to lift the patient's sternum.

The top panel 202 may also be partially defined by a lower surface 326 that is opposite to the upper surface 324, and the lower surface 326 may extend from the distal end 306 to the proximal end 308 of the panel portion 302 along the longitudinal axis 310. In the embodiment in which the upper surface 324 may be planar, the lower surface 326 may also be planar and, for example, may extend along a plane parallel to the X-Y plane of the reference coordinate system of FIG. 11G. However, as illustrated in the left side view of FIG. 11A, the lower surface 326 may have the same or similar arc or cambered shape as the upper surface 324.

Referring again to FIG. 11A, the panel member 300 may include the support portion 304 which is elongated and extends from a top end 328 to a bottom end 330 along a support axis 332 that extends parallel or substantially parallel to the Z-axis of the reference coordinate system of FIG. 11A. However, in some embodiments, support axis 332 may extend at an acute angle relative to the Z-axis of the reference coordinate system of FIG. 11A, and in other embodiments, the support axis 332 may be non-linear. The bottom end 330 of the support portion 304 may be coupled to the panel portion 302 at or adjacent to the proximal end 308 of the panel portion 302. As illustrated in FIG. 11C, an outer lateral edge 334 of the support portion 304 may be disposed at or adjacent to a portion of the first lateral edge 312 when viewed parallel to the Z-axis of the reference coordinate system of FIG. 11G, and an inner lateral edge 336 of the support portion 304 may be disposed at or adjacent to a portion of the inner lateral edge 320 of the panel portion 302 when viewed parallel to the Z-axis of the reference coordinate system of FIG. 11G. The mounting post 20, 158, which may be similar or identical to the mounting post 20, 158 previously described, may be disposed at or adjacent to the top end 328 of the support portion 304.

Various advantages of a sternal ascender assembly have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A dual panel assembly comprising:
an elongated support column extending from a top end to a bottom end along a column axis;
a top panel extending from a distal end to a proximal end along a top longitudinal axis, the top panel having an upper surface that extends from the distal end to the proximal end of the top panel;
an upper yoke portion extending between a first end and a second end along a first yoke axis, wherein the first end is coupled to a first portion of the top panel and the second end is coupled to a first portion of the support column, wherein the first portion of the top panel is at or adjacent to the proximal end of the top panel, and wherein the first portion of the support column is at or adjacent to the top end of the support column;
a bottom panel extending from a distal end to a proximal end along a bottom longitudinal axis, the bottom panel having an upper surface that extends from the distal end to the proximal end of the bottom panel, wherein the bottom longitudinal axis is parallel to the top longitudinal axis;
a lower yoke portion extending between a first end and a second end along a second yoke axis, wherein the first end is coupled to a first portion of the bottom panel and the second end is coupled to a second portion of the support column, wherein the first portion of the bottom panel is at or adjacent to the proximal end of the bottom panel; and
a mounting post extending from a portion of the upper surface of the top panel along a mounting post axis, the mounting post being configured to be coupled to a device that elevates the dual panel assembly relative to a patient,
wherein the bottom panel is configured to be inserted in an incision in the patient such that the upper surface of the bottom panel contacts an interior-facing portion of a sternum of the patient, and
wherein the top panel is configured to remain outside of and elevated from the incision of the patient to be incision to be visible by a surgeon to visualize the exact positioning and orientation of the bottom panel that is inserted in the incision of the patient.

2. The dual panel assembly of claim 1, wherein the distal end of the top panel is aligned with the distal end of the bottom panel along a first axis that is parallel to the column axis.

3. The dual panel assembly of claim 2, wherein the proximal end of the top panel is aligned with the proximal end of the bottom panel along a second axis that is parallel to the column axis.

4. The dual panel assembly of claim 1, wherein the top panel is identical to the bottom panel.

5. The dual panel assembly of claim 1, wherein a portion of the support column at the top end is aligned with a portion of the top panel at or adjacent to the proximal end of the top panel.

6. The dual panel assembly of claim 5, wherein the portion of the support column at the top end is aligned with a portion of the upper surface that is at or adjacent to the proximal end of the top panel.

7. The dual panel assembly of claim 1, wherein the column axis is substantially normal to the top longitudinal axis and the bottom longitudinal axis.

8. The dual panel assembly of claim 1, wherein the mounting post axis is substantially parallel to the column axis.

9. The dual panel assembly of claim 1, wherein the upper surface of the bottom panel has an arcuate cross-sectional shape when viewed normal to the bottom longitudinal axis.

10. The dual panel assembly of claim 1, wherein the upper surface of the bottom panel is planar.

11. The dual panel assembly of claim 1, wherein the second portion of the support column is at or adjacent to the bottom end of the support column.

12. The dual panel assembly of claim 1, wherein the lower yoke portion includes an upper extension portion, and upper post portion, and a strut portion that cooperate to define a U-shape.

13. The dual panel assembly of claim 1, wherein the first yoke axis has an arcuate shape.

\* \* \* \* \*